US009585832B2

(12) United States Patent
Tamura et al.

(10) Patent No.: US 9,585,832 B2
(45) Date of Patent: Mar. 7, 2017

(54) ORGANOPOLYSILOXANE ELASTOMER MODIFIED WITH MONO-/DIGLYCERIN DERIVATIVE, AND USE THEREFOR

(75) Inventors: Seiki Tamura, Ichihara (JP); Tatsuo Souda, Ichihara (JP); Chiichiro Hasegawa, Awara (JP); Kazuhiko Kojima, Ichihara (JP); Seiji Hori, Sabae (JP)

(73) Assignee: DOW CORNING TORAY CO., LTD., Chiyoda-Ku, Tokyo (JP)

(*) Notice: Subject to any disclaimer, the term of this patent is extended or adjusted under 35 U.S.C. 154(b) by 0 days.

(21) Appl. No.: 14/122,692

(22) PCT Filed: May 22, 2012

(86) PCT No.: PCT/JP2012/063093
§ 371 (c)(1),
(2), (4) Date: Feb. 12, 2014

(87) PCT Pub. No.: WO2012/165237
PCT Pub. Date: Dec. 6, 2012

(65) Prior Publication Data
US 2014/0194532 A1    Jul. 10, 2014

(30) Foreign Application Priority Data
May 30, 2011    (JP) ................. 2011-121097

(51) Int. Cl.
| *A61K 8/893* | (2006.01) |
| *A61K 8/892* | (2006.01) |
| *C08G 77/46* | (2006.01) |
| *C08G 77/50* | (2006.01) |
| *C08L 83/12* | (2006.01) |
| *C08L 83/14* | (2006.01) |
| *A61K 9/00* | (2006.01) |
| *A61K 47/34* | (2006.01) |
| *A61K 9/107* | (2006.01) |
| *A61Q 19/00* | (2006.01) |
| *A61K 8/895* | (2006.01) |
| *A61K 8/02* | (2006.01) |
| *A61Q 19/08* | (2006.01) |
| *A61Q 5/00* | (2006.01) |
| *C08G 77/12* | (2006.01) |

(52) U.S. Cl.
CPC ............ *A61K 8/892* (2013.01); *A61K 8/0241* (2013.01); *A61K 8/893* (2013.01); *A61K 8/895* (2013.01); *A61K 9/0014* (2013.01); *A61K 9/107* (2013.01); *A61K 47/34* (2013.01); *A61Q 5/00* (2013.01); *A61Q 19/00* (2013.01); *A61Q 19/007* (2013.01); *A61Q 19/08* (2013.01); *C08G 77/46* (2013.01); *C08G 77/50* (2013.01); *C08L 83/12* (2013.01); *C08L 83/14* (2013.01); *A61K 2800/10* (2013.01); *C08G 77/12* (2013.01); *Y10T 428/2982* (2015.01)

(58) Field of Classification Search
None
See application file for complete search history.

(56) References Cited

U.S. PATENT DOCUMENTS

| 4,222,952 | A | | 9/1980 | Vick |
| 4,515,979 | A | | 5/1985 | Otsuki et al. |
| 4,853,474 | A | | 8/1989 | Bahr et al. |
| 4,940,751 | A | | 7/1990 | Frances et al. |
| 4,987,169 | A | | 1/1991 | Kuwata et al. |
| 5,136,068 | A | | 8/1992 | Bahr et al. |
| 5,225,509 | A | | 7/1993 | Heinrich et al. |
| 5,236,986 | A | * | 8/1993 | Sakuta ............... A61K 8/894 524/267 |
| 5,288,831 | A | | 2/1994 | Ichinohe et al. |
| 5,387,417 | A | | 2/1995 | Rentsch |
| 5,654,362 | A | | 8/1997 | Schulz, Jr. et al. |
| 5,811,487 | A | | 9/1998 | Schulz, Jr. et al. |
| 5,981,680 | A | | 11/1999 | Petroff et al. |
| 6,239,244 | B1 | | 5/2001 | Stepp et al. |
| 6,509,024 | B2 | * | 1/2003 | Lorant ............... A61K 8/891 424/401 |
| 6,677,446 | B2 | | 1/2004 | Duval |
| 8,288,498 | B2 | | 10/2012 | Hayashi et al. |
| 8,546,483 | B2 | | 10/2013 | Tanaka et al. |

(Continued)

FOREIGN PATENT DOCUMENTS

| AT | 312121 T | 12/2005 |
| AT | 356845 T | 4/2007 |

(Continued)

OTHER PUBLICATIONS

Original document and English language abstract for AT 312121 not found; however see English language equivalent U.S. Pat. No. 6,677,446.
English language translation only for AT 356845 extracted from espacenet.com database on Jun. 9, 2014, 13 pages.
Original document and English language abstract for AT 526365 not found; however see English language equivalent US 2008/0138386.
Original document and English language abstract for AU 4734599 not found; however see English language equivalent U.S. Pat. No. 6,677,446.
English language abstract not found for CA 2281973; however see English language equivalent U.S. Pat. No. 6,677,446. Original document extracted from espacenet.com database one Jun. 9, 2014, 55 pages.
English language abstract for CN 101084275 extracted from espacenet.com database on Jun. 9, 2014, 40 pages.
English language abstract for CN 102257040 extracted from espacenet.com database on Jun. 10, 2014, 43 pages.
English language abstract not found for DE 3881647; however see English language equivalent U.S. Pat. No. 4,940,751. Original document extracted from espacenet.com database one Jun. 9, 2014, 25 pages.
English language abstract for DE 19711314 extracted from espacenet.com database on Jun. 9, 2014, 9 pages.

(Continued)

Primary Examiner — Brian Gulledge
(74) Attorney, Agent, or Firm — Howard & Howard Attorneys PLLC

(57) ABSTRACT

The present invention relates to a glycerin derivative-modified organopolysiloxane elastomer comprising:
as a hydrophilic group, a glycerin derivative group in which an average number of repetitions of glycerin units is in a range of 1.0 to 2.4, being free of an oxyalkylene structure having an average number of repetitions of an oxyalkylene unit of 2 or higher; and
a crosslinked three-dimensional net-like structure having a carbon-silicon bond in a crosslinking part.

25 Claims, No Drawings

(56) References Cited

U.S. PATENT DOCUMENTS

| | | | |
|---|---|---|---|
| 8,686,174 | B2 | 4/2014 | Okawa |
| 2002/0035229 | A1 | 3/2002 | Kondo et al. |
| 2003/0158363 | A1 | 8/2003 | Nakanishi |
| 2004/0068106 | A1 | 4/2004 | Duval |
| 2004/0091439 | A1 | 5/2004 | Kamei et al. |
| 2004/0146472 | A1 | 7/2004 | Nakanishi |
| 2004/0253197 | A1 | 12/2004 | Sakuta |
| 2005/0043365 | A1 | 2/2005 | Yoshitake et al. |
| 2006/0018935 | A1 | 1/2006 | Nishijima et al. |
| 2006/0034875 | A1* | 2/2006 | Nakanishi ............ A61K 8/891 424/401 |
| 2006/0165629 | A1 | 7/2006 | Kamei et al. |
| 2007/0004858 | A1 | 1/2007 | Zech et al. |
| 2008/0138386 | A1 | 6/2008 | Joffre et al. |
| 2008/0200608 | A1 | 8/2008 | Burger et al. |
| 2008/0273168 | A1 | 11/2008 | Rathore et al. |
| 2008/0311060 | A1 | 12/2008 | Sakuta et al. |
| 2009/0171057 | A1 | 7/2009 | O'Lenick et al. |
| 2009/0203802 | A1* | 8/2009 | Kamei et al. ................. 514/769 |
| 2009/0232859 | A1 | 9/2009 | Sakuta et al. |
| 2010/0113731 | A1 | 5/2010 | Hayashi et al. |
| 2010/0158824 | A1 | 6/2010 | Lin |
| 2011/0015337 | A1 | 1/2011 | Sakuta et al. |
| 2011/0251417 | A1 | 10/2011 | Okawa |
| 2012/0269747 | A1 | 10/2012 | Iimura et al. |
| 2012/0269748 | A1 | 10/2012 | Tamura et al. |
| 2012/0269875 | A1 | 10/2012 | Tamura et al. |
| 2013/0102686 | A1 | 4/2013 | Tamura et al. |

FOREIGN PATENT DOCUMENTS

| | | |
|---|---|---|
| AT | 526365 T | 10/2011 |
| AU | 4734599 A | 6/2000 |
| AU | 769244 A | 1/2004 |
| CA | 2281973 A1 | 3/2000 |
| CN | 101084275 A | 12/2007 |
| CN | 101641396 A | 2/2010 |
| CN | 102257040 A | 11/2011 |
| DE | 3881647 T2 | 10/1993 |
| DE | 19711314 A1 | 9/1998 |
| DE | 69928733 T2 | 8/2006 |
| DE | 60218891 T2 | 12/2007 |
| DE | 112008000839 T5 | 2/2010 |
| DK | 0985682 T3 | 4/2006 |
| EP | 0317377 A1 | 5/1989 |
| EP | 0381318 A2 | 8/1990 |
| EP | 0985682 A1 | 3/2000 |
| EP | 1148100 A2 | 10/2001 |
| EP | 1416016 A1 | 5/2004 |
| EP | 1512724 A1 | 3/2005 |
| EP | 2014701 A2 | 1/2009 |
| EP | 2716685 A1 | 4/2014 |
| EP | 2716686 A1 | 4/2014 |
| EP | 2716688 A1 | 4/2014 |
| ES | 2252924 T3 | 5/2006 |
| FR | 2622201 A1 | 4/1989 |
| FR | 2784108 A1 | 4/2000 |
| JP | S5541210 B2 | 10/1980 |
| JP | S594446 B2 | 1/1984 |
| JP | S6018525 A | 1/1985 |
| JP | S6268820 A | 3/1987 |
| JP | S63139106 A | 6/1988 |
| JP | S63248410 A | 10/1988 |
| JP | H01152158 A | 6/1989 |
| JP | H01207354 A | 8/1989 |
| JP | H0243263 A | 2/1990 |
| JP | H02302438 A | 12/1990 |
| JP | H04272932 A | 9/1992 |
| JP | H05140320 A | 6/1993 |
| JP | H05186596 A | 7/1993 |
| JP | H06040847 A | 2/1994 |
| JP | H06040848 A | 2/1994 |
| JP | H07041417 A | 2/1995 |
| JP | H07185212 A | 7/1995 |
| JP | H07187945 A | 7/1995 |
| JP | H07292119 A | 11/1995 |
| JP | H07330907 A | 12/1995 |
| JP | H08000908 A | 1/1996 |
| JP | H09071504 A | 3/1997 |
| JP | H09165315 A | 6/1997 |
| JP | H09165318 A | 6/1997 |
| JP | H10316536 A | 12/1998 |
| JP | H11049957 A | 2/1999 |
| JP | 2000038450 A | 2/2000 |
| JP | 2000063225 A | 2/2000 |
| JP | 2000086702 A | 3/2000 |
| JP | 2000509761 A | 8/2000 |
| JP | 2000319515 A | 11/2000 |
| JP | 2001064513 A | 3/2001 |
| JP | 2001115390 A | 4/2001 |
| JP | 2002105318 A | 4/2001 |
| JP | 2001187842 A | 7/2001 |
| JP | 2001192459 A | 7/2001 |
| JP | 2001512164 A | 8/2001 |
| JP | 2001294755 A | 10/2001 |
| JP | 2002119840 A | 4/2002 |
| JP | 2002179798 A | 6/2002 |
| JP | 2003146991 A | 5/2003 |
| JP | 2004169015 A | 6/2004 |
| JP | 2004174495 A | 6/2004 |
| JP | 2005120293 A | 5/2005 |
| JP | 2005523980 A | 8/2005 |
| JP | 2005529989 A | 10/2005 |
| JP | 2006511645 A | 4/2006 |
| JP | 2006511646 A | 4/2006 |
| JP | 2007504312 A | 3/2007 |
| JP | 2007126359 A | 5/2007 |
| JP | 4009382 B2 | 11/2007 |
| JP | 2007532754 A | 11/2007 |
| JP | 2008115358 A | 5/2008 |
| JP | 2008525598 A | 7/2008 |
| JP | 4187198 B2 | 11/2008 |
| JP | 2008274241 A | 11/2008 |
| JP | 2008542010 A | 11/2008 |
| JP | 2009262080 A | 11/2009 |
| JP | 2010120913 A | 6/2010 |
| JP | 2010144156 A | 7/2010 |
| JP | 2011049248 A | 3/2011 |
| JP | 2011121095 A | 6/2011 |
| JP | 2011121097 A | 6/2011 |
| JP | 2011246705 A | 12/2011 |
| JP | 2012246446 A | 12/2012 |
| KR | 20040038865 A | 5/2004 |
| KR | 20080042784 A | 5/2008 |
| KR | 20110087330 A | 8/2011 |
| NO | 994411 A | 3/2000 |
| WO | WO 98/41579 | 9/1998 |
| WO | WO 9906473 A1 | 2/1999 |
| WO | WO 0114458 A1 | 3/2001 |
| WO | WO 02055588 A1 | 7/2002 |
| WO | WO 03020828 A1 | 3/2003 |
| WO | WO 03042284 A1 | 5/2003 |
| WO | WO 03093349 A1 | 11/2003 |
| WO | WO 03093369 A1 | 11/2003 |
| WO | WO 2004024798 A1 | 3/2004 |
| WO | WO 2004046226 A1 | 6/2004 |
| WO | WO 2004058857 A2 | 7/2004 |
| WO | WO 2004058858 A1 | 7/2004 |
| WO | WO 2005023934 A1 | 3/2005 |
| WO | WO 2005100444 A1 | 10/2005 |
| WO | WO 2006071772 A | 7/2006 |
| WO | WO 2006090478 A2 | 8/2006 |
| WO | WO 2007061623 A1 | 5/2007 |
| WO | WO 2007109240 A2 | 9/2007 |
| WO | WO 2008123318 A1 | 10/2008 |
| WO | WO 2009006091 A2 | 1/2009 |
| WO | WO 2009/116689 A1 | 9/2009 |
| WO | WO 2010074296 A1 | 7/2010 |
| WO | WO 2011028765 A1 | 3/2011 |
| WO | WO 2011028770 A1 | 3/2011 |
| WO | WO 2011049246 A1 | 4/2011 |
| WO | WO 2011049247 A1 | 4/2011 |
| WO | WO 2011049248 A1 | 4/2011 |

(56) References Cited

FOREIGN PATENT DOCUMENTS

| WO | WO 2011136397 A1 | 11/2011 |
|---|---|---|
| WO | WO 2012165228 A1 | 12/2012 |
| WO | WO 2012165233 A1 | 12/2012 |
| WO | WO 2012165235 A1 | 12/2012 |
| WO | WO 2013100207 A1 | 7/2013 |

OTHER PUBLICATIONS

English language abstract not found for DE 60218891; however see English language equivalent US 2005/0043365. Original document extracted from espacenet.com database one Jun. 9, 2014, 14 pages.
English language abstract not found for DE 69928733; however see English language equivalent U.S. Pat. No. 6,677,446. Original document extracted from espacenet.com database one Jun. 9, 2014, 33 pages.
English language abstract not found for DE 112008000839; however see English language equivalent US 2010/0113731. Original document extracted from espacenet.com database one Jun. 9, 2014, 24 pages.
English language abstract not found for DK 0985682; however see English language equivalent U.S. Pat. No. 6,677,446. Original document extracted from espacenet.com database one Jun. 10, 2014, 52 pages.
English language abstract for EP 0317377 extracted from espacenet.com database on Jun. 10, 2014, 12 pages.
English language abstract for EP 0985682 extracted from espacenet.com database on Jun. 10, 2014, 34 pages.
English language abstract not found for ES 2252924; however see English language equivalent U.S. Pat. No. 6,677,446. Original document extracted from espacenet.com database one Jun. 10, 2014, 30 pages.
English language abstract not found for FR 2622201; however see English language equivalent U.S. Pat. No. 4,940,751. Original document extracted from espacenet.com database one Jun. 10, 2014, 25 pages.
English language abstract not found for FR 2784108; however see English language equivalent U.S. Pat. No. 6,677,446. Original document extracted from espacenet.com database one Jun. 10, 2014, 53 pages.
English language abstract not found for JP 4187198; however see English language equivalent US 2003/158363. Original document extracted from espacenet.com database one Jun. 10, 2014, 33 pages.
English language abstract for KR 20040038865 extracted from espacenet.com database on Jun. 10, 2014, 43 pages.
English language abstract for KR 20080042784 extracted from espacenet.com database on Jun. 10, 2014, 54 pages.
English language abstract not found for KR 20110087330; however see English language equivalent US 2011/0251417. Original document extracted from espacenetcom database one Jun. 10, 2014, 40 pages.
English language abstract not found for NO 994411; however see English language equivalent U.S. Pat. No. 6,677,446. Original document extracted from espacenet.com database one Jun. 9, 2014, 41 pages.
English language abstract for WO 98/41579 extracted from espacenet.com database on Jun. 10, 2014, 25 pages.
English language abstract for CN 101641396 extracted from epsacenet.com database on Jun. 9, 2014, 37 pages.
English language abstract and machine translation for JP 2007126359 extracted from espacenet.com database on May 14, 2014, 49 pages.
English language abstract not found for JP 2007504312; however, see English language equivalent WO 2005/023934. Original document extracted from espacenet.com database on May 9, 2014, 26 pages.
English language abstract not found for JP 2007532754; however, see English language equivalent WO 2005/100444. Original document extracted from espacenet.com database on May 9, 2014, 39 pages.
English language abstract for JP 2008115358 extracted from PAJ database on May 12, 2014, 1 page. English language machine translation extracted from JPO database, 146 pages.
English language abstract for JP 2008274241 extracted from PAJ database on May 12, 2014, 1 page. English language machine translation extracted from JPO database, 49 pages.
English language abstract not found for JP 2008525598; however, see English language equivalent WO 2006/071772. Original document extracted from espacenet.com database on May 9, 2014, 35 pages.
English language abstract not found for JP 2008542010; however, see English language equivalent US 2008/0200608. Original document extracted from espacenet.com database on May 9, 2014, 24 pages.
English language abstract for JP 2009262080 extracted from PAJ database on May 12, 2014, 1 pages. English language machine translation extracted from JPO database, 52 pages.
English language abstract and machine translation for JP 2010120913 extracted from espacenet.com database on May 14, 2014, 24 pages.
English language abstract for JP 2010144156 extracted from espacenet.com database on May 14, 2014, 43 pages.
English language abstract and machine translation for JP 2011049248 extracted from espacenet.com database on May 14, 2014, 25 pages.
English language abstract and machine translation for JP 2011121095 extracted from espacenet.com database on May 14, 2014, 27 pages.
English language abstract and machine translation for JP 2011121097 extracted from espacenet.com database on May 14, 2014, 18 pages.
English language abstract for JP 2011246705 extracted from espacenet.com database on May 9, 2014, 55 pages.
English language abstract for JP 2012246446 extracted from PAJ database on May 14, 2014, 1 page. English language machine translation extracted from JPO database, 278 pages.
English language abstract for WO 02/055,588 extracted from espacenet.com database on May 9, 2014, 67 pages.
English language abstract for WO 03/020,828 extracted from espacenet.com database on May 12, 2014, 65 pages.
English language abstract for WO 2004/024,798 extracted from espacenet.com database on May 12, 2014, 75 pages.
English language abstract for WO 2004/046,226 extracted from espacenet.com database on May 9, 2014, 43 pages.
English language abstract for WO 2006/090,478 extracted from espacenet.com database on May 12, 2014, 94 pages.
English language abstract for WO 2008/123,318 extracted from espacenet.com database on May 9, 2014, 40 pages.
English language abstract for WO 2011/049,246 extracted from espacenet.com database on May 14, 2014, 103 pages.
English language abstract for WO 2011/049,247 extracted from espacenet.com database on May 12, 2014, 168 pages.
English language abstract for WO 2011/049,248 extracted from espacenet.com database on May 14, 2014, 224 pages.
English language abstract for WO 2012/165,228 extracted from espacenet.com database on May 14, 2014, 127 pages.
English language abstract for WO 2012/165,235 extracted from espacenet.com database on May 14, 2014, 160 pages.
English language abstract for WO 2012/165,233 extracted from espacenet.com database on May 14, 2014, 155 pages.
International Search Report for Application No. PCT/JP2012/063086, dated Aug. 28, 2012, 6 pages.
International Search Report for Application No. PCT/JP20121063089, dated Sep. 4, 2012, 6 pages.
International Search Report for Application No. PCT/JP2012/063074, dated Sep. 11, 2012, 8 pages.
International Search Report for Application No. PCT/JP2012/063093, dated Aug. 28, 2012, 5 pages.
English language abstract for JP S5541210 extracted from JPO database, 3 pages.

(56) References Cited

OTHER PUBLICATIONS

English language abstract not found for JP S594446; however, see English language equivalent U.S. Pat. No. 4,222,952. Original document extracted from espacenet.com database on May 19, 2014, 15 pages.
English language abstract for JP S6018525 extracted from espacenet.com database on May 8, 2014, 7 pages.
English language abstract for JP S6268820 extracted from espacenet.com database on May 8, 2014, 4 pages.
English language abstract for JP S63139106 extracted from espacenet.com database on May 8, 2014, 10 pages.
English language abstract for JP S63248410 extracted from espacenet.com database on May 8, 2014, 7 pages.
English language abstract for JP H01152158 extracted from espacenet.com database on May 9, 2014, 13 pages.
English language abstract for JP H01207354 extracted from espacenet.com database on May 12, 2014, 10 pages.
English language abstract for JP H0243263 extracted from espacenet.com database on May 12, 2014, 13 pages.
English language abstract for JP H02302438 extracted from espacenet.com database on May 9, 2014, 7 pages.
English language abstract for JP H04272932 extracted from espacenet.com database on May 12, 2014, 8 pages.
English language abstract for JP H05140320 extracted from PAJ database on May 12, 2014, 1 page. English language machine translation extracted from JPO, 21 pages.
English language abstract for JP H05186596 extracted from PAJ database on May 9, 2014, 1 page. English language machine translation extracted from JPO, 32 pages.
English language abstract for JP H06040847 extracted from PAJ database on May 12, 2014, 1 page. English language machine translation extracted from JPO, 21 pages.
English language abstract for JP H06040848 extracted from PAJ database on May 12, 2014, 1 page. English language machine translation extracted from JPO, 22 pages.
English language abstract for JP H07041417 extracted from PAJ database on May 9, 2014, 1 page. English language machine translation extracted from JPO, 18 pages.
English language abstract for JP H07185212 extracted from PAJ database on May 9, 2014, 1 page. English language machine translation extracted from JPO, 20 pages.
English language abstract and machine translation for JP H07187945 extracted from espacenet.com database on May 14, 2014, 52 pages.
English language abstract for JP H07292119 extracted from PAJ database on May 9, 2014, 2 pages. English language machine translation extracted from JPO, 34 pages.
English language abstract for JP H07330907 extracted from PAJ database on May 9, 2014, 1 page. English language machine translation extracted from JPO, 16 pages.
English language abstract for JP H08000908 extracted from PAJ database on May 9, 2014, 1 page. English language machine translation extracted from JPO, 16 pages.
English language abstract for JP H09071504 extracted from PAJ database on May 14, 2014, 1 page. English language machine translation extracted from JPO, 15 pages.
English language abstract for JP H09165315 extracted from PAJ database on May 9, 2014, 1 page. English language machine translation extracted from JPO, 25 pages.
English language abstract for JP H09165318 extracted from PAJ database on May 9, 2014, 1 page. English language machine translation extracted from JPO, 25 pages.
English language abstract and machine translation for JP H10316536 extracted from espacenet.com database on May 14, 2014, 21 pages.
English language abstract for JP H11049957 extracted from PAJ database on May 12, 2014, 1 pages. English language machine translation extracted from JPO, 16 pages.
English language abstract for JP 400932 extracted from espacenet.com database on May 13, 2014, 2 pages. English language machine translation extracted from JPO, 73 pages.
English language abstract for JP 2000038450 extracted from espacenet.com database on May 9, 2014, 13 pages.
English language abstract and machine translation for JP 2000063225 extracted from PAJ database on May 9, 2014, 36 pages.
English language abstract for JP 2000086702 extracted from PAJ database on May 9, 2014, 26 pages.
English language abstract for JP 2000319515 extracted from PAJ database on May 12, 2014, 1 page. English language machine translation extracted from JPO, 32 pages.
English language abstract not found for JP 2000509761; however, see English language equivalent U.S. Pat. No. 6,239,244. Original document extracted from espacenet.com database on May 9, 2014, 22 pages.
English language abstract for JP 2001064513 extracted from PAJ database on May 12, 2014, 1 page. English language machine translation extracted from JPO, 23 pages.
English language abstract for JP 2001115390 extracted from PAJ database on May 9, 2014, 1 page. English language machine translation extracted from JPO, 20 pages.
English language abstract and machine translation for JP 2001187842 extracted from PAJ database on May 12, 2014, 22 pages.
English language abstract for JP 2001192459 extracted from PAJ database on May 12, 2014, 1 page. English language machine translation extracted from JPO, 17 pages.
English language abstract for JP 2001294755 extracted from espacenet.com database on May 9, 2014, 12 pages.
English language abstract not found for JP 2001512164; however, see English language equivalent WO 99/06473. Original document extracted from espacenet.com database on May 9, 2014, 68 pages.
English language abstract for JP 2002105318 extracted from PAJ database on May 12, 2014, 1 page. English language machine translation extracted from JPO, 69 pages.
English language abstract for JP 2002119840 extracted from PAJ database on May 9, 2014, 1 page. English language machine translation extracted from JPO, 14 pages.
English language abstract for JP 2002179798 extracted from PAJ database on May 9, 2014, 2 pages. English language machine translation extracted from JPO, 55 pages.
English language abstract and translation for JP 2003146991 extracted from PAJ database on May 9, 2014, 23 pages.
English language abstract for JP 2004169015 extracted from espacenet.com database on May 14, 2014, 43 pages.
English language abstract and translation for JP 2004174495 extracted from PAJ database on May 9, 2014, 43 pages.
English language abstract and translation for JP 2005120293 extracted from PAJ database on May 9, 2014, 117 pages.
English language abstract not found for JP 2005523980; however, see English language equivalent WO 03/093,349. Original document extracted from espacenet.com database on May 9, 2014, 45 pages.
English language abstract not found for JP 2005529989; however, see English language equivalent WO 03/093,369. Original document extracted from espacenet.com database on May 9, 2014, 54 pages.
English language abstract not found for JP 2006511645; however, see English language equivalent WO 2004/058,858. Original document extracted from espacenet.com database on May 9, 2014, 34 pages.
English language abstract not found for JP 2006511646; however, see English language equivalent WO 2004/058,857. Original document extracted from espacenet.com database on May 9, 2014, 30 pages.
"Silicones", Encyclopedia of Polymer Science and Technology, vol. 11, Wiley, pp. 765-841, Apr. 15, 2003, XP007918236.

* cited by examiner

ORGANOPOLYSILOXANE ELASTOMER MODIFIED WITH MONO-/DIGLYCERIN DERIVATIVE, AND USE THEREFOR

RELATED APPLICATIONS

This application is the National Stage of International Patent Application No. PCT/JP2012/063093, filed on May 22, 2012, which claims priority to and all the advantages of Japanese Patent Application No. JP 2011-121097, filed on May 30, 2011, the content of which is incorporated herein by reference.

TECHNICAL FIELD

The present invention relates to a specific glycerin derivative-modified organopolysiloxane elastomer having a cross-linked structure and uses for such. The glycerin derivative-modified organopolysiloxane elastomer of the present invention does not have an oxyalkylene structure having an average number of repetitions of an oxyalkylene unit of 2 or greater as a hydrophilic group. Furthermore, the applications and background art of the novel organopolysiloxane elastomer of the present invention are shared with another patent application asserting a priority right based on Japanese Patent Application No. 2011-121097 (relating to a sugar alcohol-modified organopolysiloxane elastomer and a modified organopolysiloxane elastomer having a siloxane dendron structure) filed on the same day as the present application.

BACKGROUND ART

As an organopolysiloxane elastomer having a polyether group, a silicone polymer that is swellable in silicone oil, and a paste-like silicone composition that is produced using such a silicone polymer and that is capable of being uniformly and stably disperse water have been reported (e.g. see Patent Documents 1 and 2, or the like). However, the emulsification ability, particularly the emulsification ability in non-silicone oils, of such paste-like silicone compositions have not been sufficiently satisfactory, and also the feel improvement effect of a cosmetic has been insufficient.

On the other hand, as a non-polyether type hydrophilic organopolysiloxane elastomers, an organopolysiloxane polymer having a glycerin derivative that is capable of including a liquid oil at at least a weight equivalent to the weight of the organopolysiloxane polymer, and a paste-like composition that is formed by such an organopolysiloxane elastomer swollen by including a liquid oil agent have been proposed (Patent Document 3). Moreover, Patent Document 4 proposes an organopolysiloxane elastomer characterized by a branched structure due to polydimethylsiloxyethyl groups, the organopolysiloxane elastomer further having hydrophilic groups. Among such organopolysiloxane elastomers, an organopolysiloxane elastomer is introduced that includes a glycerin derivative group as the hydrophilic group.

However, the organopolysiloxane elastomers including a glycerin derivative group investigated or reported in the practical examples of these patent documents are only polyglycerin-modified silicone elastomers or triglycerin-modified silicone elastomers, and the practical examples of these patent documents do not relate to mono-glycerin derivative-modified silicone elastomers not having an oxyalkylene structure having an average number of repetitions of an oxyalkylene unit of 2 or greater as a hydrophilic group.

Furthermore, there was no report relating to a diglycerin derivative-modified silicone elastomer not having an oxyalkylene structure having an average number of repetitions of an oxyalkylene unit of 2 or greater as a hydrophilic group.

Moreover, the organopolysiloxane elastomers including the glycerin derivative group reported or investigated in the practical examples of these documents, in comparison to a general polyether-modified silicone elastomer, as emulsifier for a water-in-oil emulsion, did not have sufficient emulsification ability with respect to a wide range of oil agents.

BACKGROUND DOCUMENTS

Patent Documents

Patent Document 1: Japanese Unexamined Patent Application Publication No. H04-272932A
Patent Document 2: Japanese Unexamined Patent Application Publication No. H05-104320A
Patent Document 3: WO2004/024798
Patent Document 4: Japanese Unexamined Patent Application Publication No. 2008-115358A

SUMMARY OF INVENTION

Technical Problem

Requests for "PEG-free formulations" have increased in recent years. For example, in Germany, a demand for the replacement of raw materials having polyether groups with non-polyether raw materials has increased due to a negative perception of the safety of products comprising polyethylene glycol (PEG) due to testing done by a consumer information magazine company. Moreover, in South Korea, increased interest in non-polyether silicone surfactants has emerged due to a concern that products containing PEG may irritate the skin because formalin may be produced as a result of oxidation degradation of PEG.

In light of the above, a global trend is assumed toward changing the entire formulation of end consumer products such as cosmetic products or the like to PEG-free formulations. In concord with this trend, also in the field of silicone-based surfactants, it is anticipated that there is need in the market for technological progression from the conventional polyether-modified silicone or polyether-modified silicone elastomer to non-polyether hydrophilic silicones or non-polyether hydrophilic silicone elastomers.

Also, in comparison to polyether-modified silicones or polyether-modified silicone elastomers, glycerin-modified silicones or glycerin-modified silicone elastomers have excellent oxidation stability, and thus such glycerin-modified silicones or glycerin-modified silicone elastomers offer promise as non-polyether hydrophilic silicones or non-polyether hydrophilic silicone elastomers.

However, conventional glycerin-modified silicones or glycerin-modified silicone elastomers have been expensive or have other major problems. That is to say, when such glycerin-modified silicones or glycerin-modified silicone elastomers are used as emulsifiers for water-in-oil emulsions, the emulsification of the glycerin-modified silicone or glycerin-modified silicone elastomer alone is low, and thus use is not possible in actual cosmetic formulations. As a result, even if there is a glycerin-modified silicone elastomer that has the advantage of excellent feel in comparison to polyether-modified silicone elastomers, and due to the lack of a polyoxyethylene (PEG) structure, that lacks the occurrence of the problem of oxidative degradation, an water-inoil emulsion cosmetic cannot be prepared that has sufficient stability without combined use together with a nonionic surfactant such as another hydrophilic silicone emulsification agent having the PEG structure or the like. It has been difficult to sufficiently realize an effect of improved feel for the overall formulation, and it has been difficult to shift the entire cosmetic to a PEG-free formulation.

The present invention is developed in order to solve the aforementioned problems. A first object of the present invention is to provide a novel glycerin derivative-modified organopolysiloxane elastomer and production method thereof, where the glycerin derivative-modified organopolysiloxane elastomer has compatibility with various types of oil agents, has excellent structural control properties and gelling properties, has further excellent lasting feel (in particular, a smooth and thick velvety sensation), that further has no stickiness whatsoever from the time of initial application until after drying, and that further has excellent beautifying effects such as wrinkle concealment (masking effect) or the like.

A second object of the present invention is to provide a novel glycerin derivative-modified organopolysiloxane elastomer and production method thereof, which while providing all the aforementioned properties, further have an excellent moisturizing effect and emulsification properties, and which in addition to the ability to emulsify silicone oils (low polarity oils) and ester oils (intermediate to high polarity oils), readily form stable emulsions using a silicone surfactant, so a stable emulsion may be formed with hydrocarbon oils (non-polar oils), which had been particularly difficult to emulsify using a conventional non-polyether type silicone surfactant, so that it becomes possible to expand the range of formulations according to object (e.g. cosmetic, external use preparation, or the like).

A third object of the present invention is to provide a raw material for an external use preparation or cosmetic (i.e. raw material such as a gelling agent, structuring agent, thickener, texture modifier, humectant, masking agent, surfactant, emulsifier, coating agent, powder dispersion stabilizer, or the like) including the aforementioned glycerin derivative-modified organopolysiloxane elastomer, as well as to provide a cosmetic or external use preparation including the glycerin derivative-modified organopolysiloxane elastomer.

A fourth object of the present invention is to provide an external use preparation or cosmetic, which by use of a raw material for an external use preparation or cosmetic including the glycerin derivative-modified organopolysiloxane elastomer, conforms to the world-wide trend that is modification of the overall composition of products intended for the end consumer (cosmetics or the like) as PEG-free formulations, the external use preparation or cosmetic not including compounds including a polyoxyethylene region.

A fifth object of the present invention is to provide a glycerin derivative-modified organopolysiloxane elastomer of reduced odor, a raw material for an external use preparation or cosmetic that includes such a glycerin derivative-modified organopolysiloxane elastomer, and an external use preparation or cosmetic that includes such a raw material.

Solution to Problem

As a result of intensive investigation aimed at achieving the above objects, the present inventors arrived at the present invention. That is to say, the first and second objects of the present invention may be attained by a glycerin derivative-modified organopolysiloxane elastomer comprising: as a hydrophilic group, a glycerin derivative group in which an average number of repetitions of glycerin units is in a range of 1.0 to 2.4, being free of an oxyalkylene structure having an average number of repetitions of an oxyalkylene unit of 2 or greater; and a crosslinked three-dimensional net-like structure having a carbon-silicon bond in a crosslinking part.

The glycerin derivative group is bonded to a silicon atom through a divalent linking group, and is preferably at least one type selected from the group consisting of glycerin units represented by the following structural formulae (4-1) to (4-3):

Formula 1

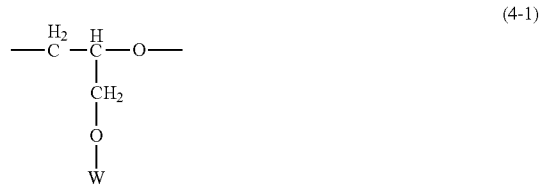
(4-1)

(in the formula, W is a hydrogen atom or an alkyl group having from 1 to 20 carbons);

Formula 2

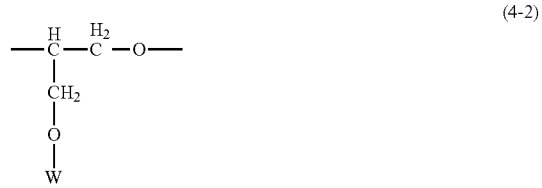
(4-2)

(in the formula, W is synonymous with the groups described above); and

Formula 3

(4-3)

the glycerin derivative group preferably includes a glycerin derivative group-containing organic group having an average number of repetitions of glycerin units in a range of 1.0 to 2.4; however, the glycerin derivative group does not have as a hydrophilic group an oxyalkylene structure having an average number of repetitions of an oxyalkylene unit of 2 or greater.

The glycerin derivative group is preferably selected from the group consisting of the following: a diglycerin derivative group represented by following general formula (5-1):

Formula 4

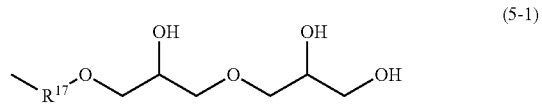
(5-1)

(in the formula, $R^{17}$ represents a divalent organic group not having an oxyalkylene structure having an average number of repetitions of an oxyalkylene unit of 2 or greater); a diglycerin derivative group represented by following general formula (5-2):

Formula 5

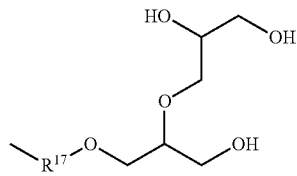

(5-2)

(in the formula, $R^{17}$ is synonymous with the groups described above); and a mono-glycerin derivative group represented by following general formula (5-3):

Formula 6

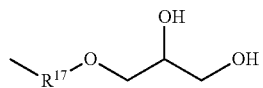

(5-3)

(in the formula, $R^{17}$ is synonymous with the groups described above).

Moreover, the first and second object of the present invention may be attained by a method for producing a glycerin derivative-modified organopolysiloxane elastomer, the method including a step of reaction of at least:
(A) an organohydrogenpolysiloxane;
(B) a glycerin derivative group-containing organic compound having a reactive unsaturated group; and
(C) at least one type of organic compound selected from the group consisting of: (C1) organic compounds having an average of greater than one reactive unsaturated group per single molecule, and (C2) organic compounds having at least one reactive unsaturated group and at least one epoxy group per single molecule.

The third and/or fourth objects of the present invention may be attained by an external use preparation raw material or cosmetic raw material, or external use preparation or cosmetic including the glycerin derivative-modified organopolysiloxane elastomer; and by a composition including at least one type of oil agent in addition to the glycerin derivative-modified organopolysiloxane elastomer; and by an external use preparation raw material or cosmetic raw material, or external use preparation or cosmetic including the composition. The composition is preferably an emulsion or paste.

The fourth object of the present invention in particular may be suitably attained by the external use preparation or cosmetic that does not include a compound having an oxyalkylene structure having an average number of repetitions of an oxyalkylene unit of 2 or greater, and that particularly preferably does not include a compound having a polyoxyethylene group or polyoxyethylene part, as a hydrophilic group, while including an external use preparation or cosmetic containing the glycerin derivative-modified organopolysiloxane elastomer, and preferably containing the glycerin derivative-modified organopolysiloxane elastomer.

The fifth object of the present invention may be attained by an organopolysiloxane elastomer obtained by the production method for the glycerin derivative-modified organopolysiloxane elastomer, or by the glycerin derivative-modified organopolysiloxane elastomer obtained by, after adding at least one type of acidic substance for treatment to a composition including at least one type of oil agent as well as the glycerin derivative-modified organopolysiloxane elastomer, heating or reducing pressure to remove volatile components. The fifth object of the present invention may also be attained by a composition of the glycerin derivative-modified organopolysiloxane elastomer, or by an external use preparation raw material or cosmetic raw material, or external use preparation or cosmetic including the glycerin derivative-modified organopolysiloxane elastomer or the composition comprising the same.

Advantageous Effects of Invention

According to the present invention, it is possible to provide a novel organomodified organopolysiloxane elastomer that has compatibility with various types of oil agents; that has excellent emulsification characteristics, thickening characteristics, gelling characteristics, and structural control characteristics; that further imparts excellent sensation, particularly by thick and velvety smoothness, with little stickiness when drying; the novel organomodified organopolysiloxane elastomer not having an oxyalkylene structure having an average number of repetitions of an oxyalkylene unit of 2 or greater as the hydrophilic group.

Moreover, the organomodified organopolysiloxane elastomer of the present invention is able to bring about excellent beautifying effects such as a wrinkle-concealing effect, moisturizing effect, or the like.

Also, the organomodified organopolysiloxane elastomer of the present invention has excellent emulsification characteristics, and it is possible to realize excellent emulsification performance for non-polar hydrocarbon oils, not just for low polarity silicone oils and intermediate-high polarity ester oils. Thus, by blending the organomodified organopolysiloxane elastomer of the present invention in an external use preparation or cosmetic, it is possible to design external use preparations or cosmetics of various type of formulations. Furthermore, the external use preparation or cosmetic of the present invention can be used as an external use preparation or cosmetic that does not require including a compound having a polyoxyethylene group or a polyoxyethylene region, such as a polyether-modified silicone. This conforms to the world-wide trend that is modification of the overall composition of products intended for the end consumer (cosmetics or the like) as PEG-free formulations, and thus the it is possible to attain an external use preparation or cosmetic not including compounds having a polyoxyethylene region. The organopolysiloxane elastomer of the present invention can be used to prepare a water-in-oil emulsion cosmetic or the like having sufficient stability, even without combined use with a nonionic surfactant such as a hydrophilic silicone emulsifier or the like having a PEG structure. The formulation of the cosmetic or external use preparation may be formulated as an overall PEG-free formulation (i.e. formulation that does not include a compound having a polyoxyethylene (PEG) structure). That is to say, by use of the organopolysiloxane elastomer of the present invention, it is possible to realize a business strategy that is highly suitable for the environment due to being in accord with the world-wide trend for entirely PEG-free is formulations for product formulations targeting the end consumer (i.e. cosmetics or the like).

Further, a composition containing the organomodified organopolysiloxane elastomer of the present invention can maintain contradictory characteristics in that feel is extremely soft while the composition also has stably maintainable high viscosity. This effect is remarkable when the organomodified organopolysiloxane elastomer is in the particulate form.

Furthermore, the organomodified organopolysiloxane elastomer of the present invention has an excellent effect in maintaining the dispersed state of a powder dispersed in a medium, and the organomodified organopolysiloxane elastomer is able to particularly improve storage stability of a composition that includes powders.

Due to the functions of the organomodified organopolysiloxane elastomer of the present invention, the organomodified organopolysiloxane elastomer of the present invention can be used suitably as a raw material for an external use preparation or cosmetic such as a thickener, gelling agent, structuring agent, texture modifier, humectant, masking agent, surfactant, emulsifier, coating agent, powder dispersion stabilizer, or the like. Moreover, the organomodified organopolysiloxane elastomer of the present invention can be suitably blended in a cosmetic or external use preparation. It is particularly possible to provide a non-aqueous type emulsion composition that has excellent stability and is capable of being used as a drug delivery system, and it is possible to provide a water-in-oil or oil-in-water emulsion composition that similarly has excellent stability.

Moreover, the organomodified organopolysiloxane elastomer of the present invention can be blended uniformly with a wide variety of oil agents, and thus the organomodified organopolysiloxane elastomer can be used to form a composition with various types of oil agents. Furthermore, a composition comprising an oil agent in conjunction with the organomodified organopolysiloxane elastomer of the present invention has superior storage stability.

The odor of the organomodified organopolysiloxane elastomer may be decreased according to the present invention. The odor-reduced organomodified organopolysiloxane elastomer of the present invention is suitable as a raw material for external use preparations and cosmetics, and is particularly suitable as a component of external use preparations and cosmetics. According to the present invention, it is possible to provide an organomodified organopolysiloxane elastomer or the composition comprising the same that is substantially odorless or that has suppressed odor generation at high temperature or over a long time interval, and it is possible to provide such an organomodified organopolysiloxane elastomer or the composition comprising the same by a simple step, such as an acid treatment. Features of the present invention are that the present invention is advantageous for implementation on an industrial scale, the ability to easily provide a reduced-odor organomodified organopolysiloxane elastomer or the composition comprising the same at low cost.

Moreover, when the odor-reduced organomodified organopolysiloxane elastomer of the present invention is blended in an external use preparation or cosmetic, there is no need for masking of odor, and the design of the formulation of the external use preparation or cosmetic has a high degree of freedom. This is particularly advantageous in cosmetic compositions, in which functions that contain an odor are emphasized.

DETAILED DESCRIPTION OF THE INVENTION

Glycerin Derivative-Modified Organopolysiloxane Elastomer and Production Method Thereof The first embodiment of the present invention is a glycerin derivative-modified organopolysiloxane elastomer comprising: as a hydrophilic group, a glycerin derivative group in which an average number of repetitions of glycerin units is in a range of 1.0 to 2.4, being free of an oxyalkylene structure having an average number of repetitions of an oxyalkylene unit of 2 or greater; and a crosslinked three-dimensional net-like structure having a carbon-silicon bond in a crosslinking part.

The glycerin derivative-modified organopolysiloxane elastomer of the present invention is an elastomer that has a relatively high crosslinking density. The glycerin derivative-modified organopolysiloxane elastomer of the present invention is an insoluble gel, gum, or powdery solid in a solvent or the like. This organopolysiloxane elastomer preferably has no fluidity at 25° C., i.e. is preferably in a non-liquid state. The expression "has no fluidity at 25° C." is taken to mean that, when the organopolysiloxane elastomer has been introduced into a certain container, and then the surface of the organopolysiloxane elastomer is made horizontal using a trowel of the like, after the container is tilted, the surface does not become horizontal again after 24 hours have passed. Here, the term "horizontal" is taken to mean forming a flat surface that is perpendicular to the direction of action of gravity.

Moreover, the organopolysiloxane elastomer of the present invention has a crosslinked three-dimensional net-like structure provided with a crosslinking part including a carbon-silicon bond. The crosslinked three-dimensional net-like structure also includes a polysiloxane chain. However, the organopolysiloxane elastomer of the present invention has a highly crosslinked molecular structure in which the polysiloxane chains are crosslinked in the three-dimensional net-like structure at relatively high density. Thus, the organopolysiloxane is an insoluble gel, gum, or powdery solid in a solvent or the like.

The glycerin derivative-modified organopolysiloxane elastomer of the present invention is preferably capable of swelling by incorporating an amount of an oil agent that is at least the weight of the glycerin derivative-modified organopolysiloxane elastomer itself. This organopolysiloxane elastomer including the oil agent made exist in the form of a paste. Examples of the oil agent types or the like are explained below, although the oil agent is preferably a silicone oil.

The glycerin derivative-modified organopolysiloxane elastomer of the present invention is characterized as not having as a hydrophilic group an oxyalkylene structure having an average number of repetitions of an oxyalkylene unit of 2 or greater, and as having glycerin derivative groups where the average number of repetitions of glycerin units is in a range of 1.0 to 2.4. Furthermore, a hydrophilic group or hydrophilic structure is a functional group or a molecular structure that imparts hydrophilicity to an organopolysiloxane molecule, and generally is a functional group or a structure derived from a hydrophilic compound.

In particular, in the present invention, it is essential to satisfy the condition that the average value of the number of repetitions of glycerin units in a molecule is in a range from 1.0 to 2.4, and if a glycerin derivative group does not satisfy the condition, it is not preferable because the emulsification performance drops. Furthermore, in the present invention, an oxyalkylene derivative group containing an oxyalkylene structure wherein an average value of the number of repetitions of the oxyalkylene unit is two or more in a molecule, or a structure similar thereto, must not be present as a hydrophilic group. Here, the oxyalkylene structure as the hydrophilic group contains a molecular internal structure (—(OC$_2$H$_4$)$_n$—, in the formula, n is a number having a value of at least 2) containing a polyoxyethylene unit having an average number of repetitions of oxyethylene units of at least two, or alternatively, the oxyalkylene structure is an oxyalkylene derivative group having a hydroxyl group (—OH), and a structure of repeated oxyalkylene units of at least two carbons each (e.g. the group represented by —(OC$_m$H$_{2m}$)$_n$—OH; in the formula, m and n are each independently numbers of at least two). In particular, if a polyoxyalkylene-modified group containing a polyoxyalkylene structure or a structure similar thereto is present in the molecule as a hydrophilic group, it is not possible to achieve the objective of the present invention, that is, substantially improving the problem of oxidative degradation of polyoxyethylene (PEG). In addition, if the polyoxyalkylene-modified group is contained in the molecule as a hydrophilic group, it is impossible to suppress the oiliness, stickiness, or the like of a cosmetic composition, and especially a water-in-oil emulsion cosmetic composition, that contains polyoxyalkylene-modified group and the feeling to touch of the composition can significantly deteriorate compared to a case in which only a glycerin derivative group is contained as a hydrophilic group. On the other hand, a polyoxyalkylene structure that has no hydroxyl group and that is formed from polyoxyalkylene derivative groups composed of a repeating structure of only oxyalkylene units of 3 or more carbons each, or is formed from only a repeating structure of oxyalkylene units of at least 3 carbons each formed between Si, does not have properties as a hydrophilic group, and differs from a structure including oxyethylene units (i.e. is a non-PEG structure). Thus such a polyoxyalkylene structure is not prevented from being included in the molecule of the organopolysiloxane elastomer of the present invention.

The second feature of the glycerin derivative-modified organopolysiloxane elastomer of the present invention is that the glycerin derivative-modified organopolysiloxane elastomer has a glycerin derivative group as a hydrophilic group in the molecule. In the diglycerin derivative group, the average value of the number of repetitions of the glycerin unit is in a range from 1.0 to 2.4, and the average value of the number of repetitions is preferably in a range from 1.4 to 2.3, more preferably in a range from 1.8 to 2.2, and most preferably an average of 2. When the average number of repetitions of glycerin units is less than the aforementioned lower limit or exceeds the upper limit, the emulsion dispersion ability and the emulsion stability maintenance ability of the glycerin derivative-modified organopolysiloxane elastomer worsen, it becomes particularly difficult to treat an oil phase including an organic oil, and it is impossible to obtain a stable water-in-oil emulsion composition.

The number of repetitions of the glycerin unit may be an average value. A content of the diglycerin derivative group in which the number of repetitions of the glycerin unit is 2 is preferably more than 30 wt. %, more preferably 50 wt. % or more, and even more preferably 80 wt. % or more, with respect to all of the other glycerin derivative groups. Most preferable is a pure form in which purity of the diglycerin derivative group is greater than 98 wt. %. That is, the glycerin derivative-modified silicone of the present invention has an average number of repetitions of a glycerin unit that falls within the above-mentioned range, may be a hydrophilic group that contains mainly a group in which the average number of repetitions is 2, and may be a hydrophilic group that contains only a high purity diglycerin moiety.

This type of glycerin derivative group preferably includes a glycerin derivative group-containing organic group which is bonded to a silicon atom via a linking group that is at least divalent and which contains an average of 1.4 to 2.3 of one or more glycerin units selected from the glycerin units represented by following structural formulae (4-1) to (4-3) (but which does not have an oxyalkylene structure having an average number of repetitions of an oxyalkylene unit of 2 or greater in the same functional group). Note that the preferable range of the number of repetitions of each glycerin unit is the same as that described above.

Formula 7

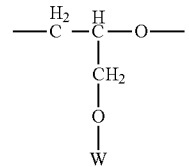

(4-1)

(in the formula, W represents a hydrogen atom or an alkyl group having from 1 to 20 carbons)

Formula 8

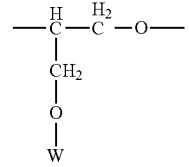

(4-2)

(in the formula, W is a group synonymous with the groups described above)

Formula 9

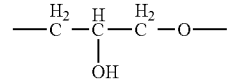

(4-3)

In formulae (4-1) to (4-3), W is preferably a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The glycerin derivative group has an average value of the number of repetitions of a glycerin unit of 1.0 to 2.4, and more preferably 2, and preferably does not contain a branch in the glycerin unit repeating structure, but it is possible for a part of the structure to be branched, such as a part of the structure being a polyglycerol group or a polyglycidylether group.

The divalent linking group is contained in the glycerin derivative group, is a bonding site to a silicon atom, and is a divalent organic group that does not contain an oxyalkylene structure wherein an average value of the number of repetitions of the oxyalkylene unit is two or more. Specifically, the divalent linking group is, for example, a straight or branched alkylene group such as an ethylene group, propylene group, butylene group and hexylene group; an alkylene phenylene group such as an ethylene phenylene group and a propylene phenylene group; an alkylene aralkylene group such as an ethylene benzylene group; an alkylenoxyphenylene group such as an ethylenoxyphenylene group and a propylenoxyphenylene group; or an alkylenoxybenzylene group such as a methylenoxybenzylene group, ethylenoxybenzylene group, and propylenoxybenzylene group. Preferable examples include groups selected from the divalent organic groups represented by the following general formula:

Formula 10

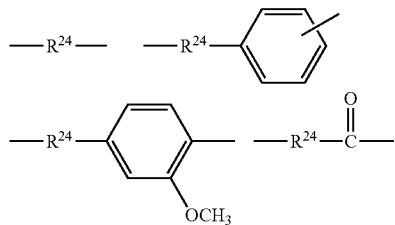

In the formulae, $R^{24}$ may have a substituent, and is each independently a straight or branched chain alkylene group or alkenylene group having from 2 to 22 carbons, or an arylene group having from 6 to 22 carbons.

The glycerin derivative group more preferably has the following structural formula (5):

$$-R^{17}-O-X_m-H \quad (5)$$

(In the formula, $R^{17}$ is a divalent organic group that does not contain an oxyalkylene structure wherein an average value of the number of repetitions of the oxyalkylene unit is two or more, and examples thereof include groups similar to the aforementioned divalent linking groups. X is at least one type of glycerin unit selected from the glycerin units represented by the structural formulae (4-1) to (4-3). m represents the number of repetitions of the glycerin unit, and is on average, a number in a range from 1.0 to 2.4. Note that the preferable range of the number of repetitions of each glycerin unit is the same as that described above).

Most preferably, the diglycerin derivative group is selected from the following: the following general formula (5-1):

Formula 11

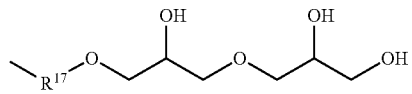

(in the formula, $R^{17}$ is a divalent organic group that does not contain an oxyalkylene structure wherein an average value of the number of repetitions of the oxyalkylene unit is two or more); or the following general formula (5-2):

Formula 12

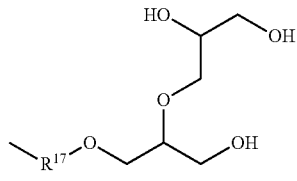

(in the formula, $R^{17}$ is synonymous with that described above); and a mono-glycerin derivative group represented by the following general formula (5-3):

Formula 13

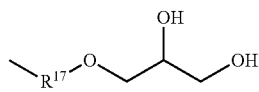

(in the formula, $R^{17}$ is synonymous with that described above).

In the glycerin derivative-modified organopolysiloxane elastomer according to the present invention, the glycerin derivative group is preferably a hydrophilic group derived from diglycerin monoallyl ether or diglyceryl eugenol. Moreover, the mono-glycerin derivative group is preferably a hydrophilic group derived from a mono-glycerin monoallyl ether and monoglyceryl eugenol.

The bond position of the glycerin derivative group can be either the terminal or side chain of polysiloxane, which is the main chain; and the structure may have two or more glycerin derivative-containing organic groups per molecule of glycerin derivative-modified organopolysiloxane elastomer, and this structure is preferable. Furthermore, these two or more glycerin derivative group-containing organic groups can be structured such that bonding occurs only in a side chain of polysiloxane, which is the main chain, only at a terminal, or in a side chain and at a terminal.

The glycerin derivative-modified organopolysiloxane elastomer of the present invention may be produced by reacting:
(A) an organohydrogenpolysiloxane;
(B) a glycerin derivative group-containing organic compound having a reactive unsaturated group; and
(C) at least one type of organic compound selected from the group consisting of: (C1) organic compounds having an average of greater than one reactive unsaturated group per single molecule, and (C2) organic compounds having at least one reactive unsaturated group and at least one epoxy group per single molecule.

No particular limitation is placed on the (A) organohydrogenpolysiloxane as long as the organohydrogenpolysiloxane has silicon atoms hydrogen atoms. This organohydrogenpolysiloxane has an average of more than one such silicon-bonded hydrogen atom, preferably has on average of 1.01 to 100 silicon-bonded hydrogen atoms, more preferably has on average of 1.1 to 50 silicon-bonded hydrogen atoms, further preferably has on average of 1.2 to 25 silicon-bonded hydrogen atoms, and particularly preferably has on average of 1.3 to 10 silicon-bonded hydrogen atoms in a single molecule. The utilized organopolysiloxane part of the organohydrogenpolysiloxane may be straight, branched, or net-like. The positions of the silicon-bonded hydrogen atoms in the organohydrogenpolysiloxane is not limited, and can be on the main chain or at the terminals. The organohydrogenpolysiloxane of the component (A) may be one type or may be a combination of two or more types.

Examples of component (A) include 1,1,3,3-tetramethyldisiloxane, 1,3,5,7-tetramethylcyclotetrasiloxane, methylhydrogenpolysiloxanes capped at both molecular terminals with trimethylsiloxy groups, copolymers of dimethylsiloxane and methyl hydrogen siloxane capped at both molecular terminals with trimethylsiloxy groups, dimethylsiloxane capped at both molecular terminals with dimethylhydrogensiloxy groups, dimethylpolysiloxane capped at both molecular terminals with dimethylhydrogensiloxy groups, copolymers of dimethylsiloxane and methylhydrogensiloxane capped at both molecular terminals with dimethylhydrogensiloxy groups, copolymers of methylhydrogensiloxane and diphenylsiloxane capped at both molecular terminals with trimethylsiloxy groups, copolymers of methylhydrogensiloxane, diphenylsiloxane and dimethylsiloxane capped at both molecular terminals with trimethylsiloxy groups, copolymers comprising a $(CH_3)_2HSiO_{1/2}$ unit and a $SiO_{4/2}$ unit, and copolymers comprising a $(CH_3)_2HSiO_{1/2}$ unit, a $SiO_{4/2}$ unit and a $(C_6H_5)SiO_{3/2}$ unit.

The component (A) is preferably a component represented by the average composition formula (1):

$$R^1_a H_b SiO_{(4-a-b)/2} \quad (1)$$

(in the formula, $R^1$ is each independently a monovalent organic group; $1.0 \leq a \leq 3.0$; and $0.001 \leq b \leq 1.5$).

No limitation is placed on the molecular structure of the (A) organohydrogenpolysiloxane, and this molecular structure is exemplified by straight, partially branched straight, branched, cyclic, and dendritic structures. This molecular structure is preferably straight. Further, no particular limitation is placed on molecular weight, and organohydrogenpolysiloxanes may be used ranging from low molecular weight organohydrogenpolysiloxanes to high molecular weight organohydrogenpolysiloxanes. Specifically, the number-average molecular weight is preferably in a range of 100 to 1,000,000, and further preferably is in a range of 300 to 500,000.

This type of organohydrogenpolysiloxane is exemplified by organohydrogenpolysiloxanes represented by the following structural formulae:

$$R^1_3SiO(R^1_2SiO)_v(R^1SiHO)_wSiR^1_3 \quad (i)$$

$$HR^1_2SiO(R^1_2SiO)_v(R^1SiHO)_zSiR^1_3 \quad (ii)$$

$$HR^1_2SiO(R^1_2SiO)_v(R^1SiHO)_zSiR^1_2H \quad (iii)$$

(in the formulae, $R^1$ is synonymous with that described above; v is 0 or a positive integer; w is a positive integer, and z is 0 or a positive integer). These organohydrogenpolysiloxanes are straight organohydrogenpolysiloxanes having silicon-bonded hydrogen atoms (i) only on the side chains, (ii) on the side chains or one terminal of the molecular chain, or (iii) on the side chains and at both terminals of the molecular chain.

No particular limitation is placed on the monovalent organic group, but the monovalent organic group is preferably a functional group selected from the below listed (D1) to (D9):

(D1) substituted or unsubstituted, straight or branched monovalent hydrocarbon groups having from 1 to 60 carbons;
(D2) a polyoxyalkylene group represented by $-R^8O(AO)_zR^9$ (wherein, AO represents an oxyalkylene group having from 3 to 4 carbons; $R^8$ represents a substituted or unsubstituted, straight or branched divalent hydrocarbon group having from 3 to 5 carbons; $R^9$ represents a substituted or unsubstituted, straight or branched monovalent hydrocarbon group having from 1 to 24 carbons, or a substituted or unsubstituted, straight or branched acyl group having from 2 to 24 carbons; and z=1 to 100);
(D3) a substituted or unsubstituted, straight or branched alkoxy group having from 1 to 30 carbons;
(D4) a hydroxyl group;
(D5) an ester group represented by $-R^{10}-COOR^{11}$ (wherein, $R^{10}$ represents a substituted or unsubstituted, straight or branched divalent hydrocarbon group having from 2 to 20 carbons; and $R^{11}$ represents a substituted or unsubstituted, straight or branched monovalent hydrocarbon group having from 1 to 30 carbons);
(D6) an ester group represented by $-R^{12}-OCOR^{13}$ (wherein, $R^{12}$ represents a substituted or unsubstituted, straight or branched divalent hydrocarbon group having from 2 to 20 carbons; and $R^{13}$ represents a substituted or unsubstituted, straight or branched monovalent hydrocarbon group having from 1 to 30 carbons);
(D7) an alkyl group substituted by a straight polysiloxane structure and represented by the following general formula (4):

Formula 14

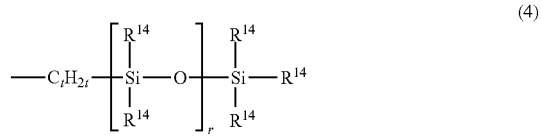

(wherein, $R^{14}$ is each independently a substituted or unsubstituted, straight or branched monovalent hydrocarbon group having from 1 to 30 carbons, a hydroxyl group, or hydrogen atom, at least one of the $R^{14}$ moieties being the monovalent hydrocarbon group; t is a number in a range of 2 to 10; and r is a number in a range of 1 to 100); (D8) an epoxy group represented by the following general formula (5):

Formula 15

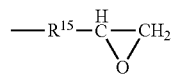

(wherein, $R^{15}$ represents a substituted or unsubstituted, straight or branched divalent hydrocarbon group having from 2 to 20 carbons); and
(D9) an alicyclic epoxy group represented by the following general formula (6):

Formula 16

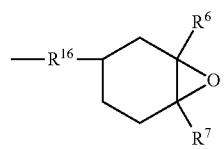

(wherein, $R^{16}$ represents a substituted or unsubstituted, straight or branched divalent hydrocarbon group having from 2 to 20 carbons; and $R^6$ and $R^7$ are synonymous with those described above).

Examples of the substituted or unsubstituted, straight or branched monovalent hydrocarbon group of (D1), (D2), (D5), (D6), and (D7) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like. The monovalent hydrocarbon group is preferably a group other than an alkenyl group, and is more preferably a methyl group, an ethyl group, or a phenyl group.

Examples of the substituted or unsubstituted, straight or branched divalent hydrocarbon group in (D5), (D6), (D8), and (D9) are as previously described.

The substituted or unsubstituted, straight or branched alkoxy group in (D3) is exemplified by the lower alkoxy groups such as the methoxy group, ethoxy group, isopropoxy group, butoxy group and the like; and higher alkoxy groups such as the lauryl alkoxy group, myristyl alkoxy group, palmityl alkoxy group, oleyl alkoxy group, stearyl alkoxy group, behenyl alkoxy group, and the like.

The (B) glycerin derivative group-containing organic compound having a reactive unsaturated group is preferably a mono- or di-glycerin derivative that has a carbon-carbon double bond at the terminals of the molecular chain. Such compounds are mono- or di-glyceride derivatives having reactive functional groups, such as alkenyl groups, at the molecular chain terminals, e.g. allyl mono-glycerol (monoglycerin monoallyl ether), allyl diglycerol (diglycerin monoallyl ether), or the like. Such compounds may be synthesized by known methods.

From the standpoints of emulsification characteristics and compatibility to oil agents, and the use as various types of treatment agents (i.e. surfactants or surface treatment agents), and especially from the standpoint of use as a powder treatment agent and use as a cosmetic raw material, in the glycerin derivative-modified organopolysiloxane elastomer of the present invention, the component (B) is specifically mono-glycerin monoallyl ether, monoglyceryl eugenol, diglycerin monoallyl ether, or diglyceryl eugenol. Diglycerin monoallyl ether or diglyceryl eugenol is particularly preferred. The preferred structure of the glycerin residue part of the glycerin derivative group, the structure of the compounds for imparting the suitable derivative group, and the like are as described above.

No structural limitation is placed on the (C1) organic compounds having an average of greater than one reactive unsaturated group per single molecule used as the component (C), as long as the average number of reactive unsaturated groups in a single molecule is greater than one, preferably is 1.01 to 10, further preferably is 1.2 to 8, still further preferably is 1.5 to 6, and particularly preferably is 2.0 to 4.5. The reactive unsaturated group preferably has a carbon-carbon double bond. The utilized organic compound may be straight, branched, or have a net-like structure, without particular limitation. Moreover, the reactive unsaturated group included in (C1) may be a general unsaturated aliphatic hydrocarbon group such as an alkenyl group or the like, or may be a hetero atom-containing unsaturated aliphatic hydrocarbon group such as the methacryl group or the like. This organic compound is preferably an organopolysiloxane or unsaturated aliphatic hydrocarbon. No particular limitation is placed on the position of the reactive unsaturated group in the organic compound, preferably the organopolysiloxane or unsaturated aliphatic hydrocarbon, and this reactive unsaturated group may be located on the main chain or on the chain terminal. However, from the standpoint of ease of control of crosslinking density, a high purity compound having two reactive unsaturated groups located at, for example, both terminals in a single molecule is preferably used.

The reactive unsaturated group preferably is present in an unsaturated aliphatic hydrocarbon group. The unsaturated aliphatic hydrocarbon group preferably has from 2 to 30 carbons, and further preferably has from 2 to 20 carbons. Examples of the monovalent unsaturated aliphatic hydrocarbon group having from 2 to 30 carbons include straight or branched alkenyl groups such as vinyl groups, 1-propenyl groups, allyl groups, isopropenyl groups, 1-butenyl groups, 2-butenyl groups, pentenyl groups, hexenyl groups, and the like; cycloalkenyl groups such as cyclopentenyl groups, cyclohexenyl groups, and the like; cycloalkenylalkyl groups such as cyclopentenylethyl groups, cyclohexenylethyl groups, cyclohexenylpropyl groups, and the like; and alkynyl groups such as ethynyl groups, propargyl groups, and the like. Alkenyl groups are preferred, and the vinyl group and hexenyl group are particularly preferred.

When the component (C1) is an organopolysiloxane, reactive unsaturated group-containing unsaturated aliphatic hydrocarbon group, reactive unsaturated group-containing hetero atom-containing unsaturated aliphatic hydrocarbon group, or the like is preferably bonded to a silicon atom. Moreover, when the component (C1) is an organopolysiloxane, the group bonded to the silicon atoms that are not the aforementioned unsaturated aliphatic hydrocarbon group or the like may be a substituted or unsubstituted monovalent hydrocarbon group or may be a monovalent organic group having a reactive functional group.

Substituted or unsubstituted monovalent hydrocarbon groups are typically substituted or unsubstituted, straight or branched monovalent saturated hydrocarbon groups having from 1 to 30 carbons, preferably from 1 to 10 carbons, and more preferably from 1 to 4 carbons, and substituted or unsubstituted monovalent aromatic hydrocarbon groups having from 6 to 30 carbons, and more preferably from 6 to 12 carbons. Moreover, component (C1) may contain, as a monovalent organic group, a hydroxyl group or an alkoxy group having from 1 to 12 carbons, such as a methoxy group, an ethoxy group, a propoxy group or a butoxy group.

Examples of the monovalent saturated hydrocarbon group having from 1 to 30 carbons include straight or branched alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like.

Examples of the monovalent aromatic hydrocarbon group having from 6 to 30 carbons include aryl groups such as phenyl groups, tolyl groups, xylyl groups, mesityl groups, and the like. Of these, a phenyl group is preferable. Note that, in the present specification, "aromatic hydrocarbon group" also includes groups in which an aromatic hydrocarbon and a saturated aliphatic hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

Hydrogen atoms in the above-mentioned monovalent hydrocarbon groups may be substituted by one or more substituted groups, and said substituted groups may be selected from the group consisting of, for example, a halogen atom (a fluorine atom, a chlorine atom, a bromine atom, or an iodine atom), a hydroxyl group, an amide group, an ester group, a carboxyl group, and an isocyanate group. A monovalent saturated or aromatic hydrocarbon group having at least one of the above-mentioned substituted groups is preferred. Specifically, it is possible to use a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatopropyl group and the like.

Examples of monovalent organic groups having reactive functional groups include monovalent saturated or aromatic hydrocarbon groups having reactive functional groups selected from the group consisting of, for example, hydroxyl groups, mercapto groups, epoxy groups, amino groups, amide groups, ester groups, carboxyl groups, and isocyanate groups. One or a plurality of reactive functional groups may exist in the monovalent organic group. The monovalent organic group is preferably a monosaturated or aromatic hydrocarbon group having at least one of the reactive functional groups described above. Specific examples of the reactive functional group include 3-hydroxypropyl groups, 3-(2-hydroxyethoxy)propyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl) ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, 3-isocyanate propyl groups, and the like.

Component (C1) is preferably a straight or branched polysiloxane. A straight polysiloxane of component (C1) is preferably a polymer that contains a diorganosiloxane unit and a triorganosiloxy unit, examples of which include dimethylpolysiloxanes capped at both molecular terminals with dimethylvinylsiloxy groups, copolymers of dimethylsiloxane and methylphenylsiloxane capped at both molecular terminals with dimethylvinylsiloxy groups, copolymers of dimethylsiloxane and methylvinylsiloxane capped at both molecular terminals with dimethylvinylsiloxy groups, copolymers of dimethylsiloxane and methylvinylsiloxane capped at both molecular terminals with trimethylsiloxy groups, copolymers of dimethylsiloxane, methylvinylsiloxane and methylphenylsiloxane capped at both molecular terminals with trimethylsiloxy groups, copolymers of dimethylsiloxane and methylvinylsiloxane capped at both molecular terminals with silanol groups, polymers in which some of the methyl groups in these polymers are substituted by alkyl groups other than methyl groups, such as ethyl groups or propyl groups, or halogenated alkyl groups such as 3,3,3-trifluoropropyl groups, and mixtures of two or more of these polymers, with straight diorganopolysiloxanes having unsaturated aliphatic hydrocarbon groups, and especially alkenyl groups, at both molecular terminals only being particularly preferred.

It is particularly preferable for a branched chain polysiloxane of component (C1) to be a polymer that contains a diorganosiloxane unit, an organosilsesquioxane unit, and a triorganosiloxy unit. The preferred silicon-bonded organic groups in these units include substituted or unsubstituted monovalent hydrocarbon groups such as alkyl groups such as the methyl group, ethyl group, propyl group, and the like; alkenyl groups such as the vinyl group, allyl group, butenyl group, hexenyl group, and the like; hetero atom-containing unsaturated aliphatic hydrocarbon groups such as the methacryl group and the like; aryl groups such as the phenyl group, tolyl group, and the like; and halogenated alkyl groups such as the 3,3,3-trifluoropropyl group and the like. Although there may be a trace amount of hydroxyl groups as well as alkoxy groups such as the methoxy group and the like, in this polymer, an average of greater than one silicon-bonded organic group needs to be a reactive unsaturated group, preferably an unsaturated aliphatic hydrocarbon group, and particularly preferably an alkenyl group. In addition, the proportions of these units are not limited, but in this polymer, it is preferable for diorganosiloxane units to account for in a range of 80.00 to 99.65 mol %, and organosilsesquioxane units to account for in a range of 0.10 to 10.00 mol %, with the balance comprising triorganosiloxy units.

The (C1-5) reactive unsaturated group-containing silicone compound represented by the average composition formula (2-4) is cited as the component (C1):

$$R^2_p R^3_q SiO_{(4-p-q)/2} \qquad (2\text{-}4)$$

(in the formula, $R^2$ may be each independently monovalent organic group that differs from $R^3$;
$R^3$ is each independently monovalent unsaturated aliphatic hydrocarbon group having from 2 to 30 carbons; $1.0 \leq p \leq 2.5$; and $0.001 \leq q \leq 1.5$). Examples of the monovalent unsaturated aliphatic hydrocarbon group having from 2 to 30 carbons are as described above.

In the average composition formula (2-4), no particular limitation is placed on the monovalent organic group of $R^2$. However, $R^2$ is preferably selected from the following (E1) to (E6) groups:
(E1) substituted or unsubstituted, straight or branched monovalent hydrocarbon groups having from 1 to 60 carbons (with the exception of monovalent hydrocarbon groups having from 2 to 20 carbons having an aliphatic unsaturated group);
(E2) a hydroxyl group;
(E3) an ester group represented by —$R^{10}$—$COOR^{11}$ (in the formula, $R^{10}$ and $R^{11}$ are as described above);
(E4) an ester group represented by —$R^{12}$—$OCOR^{13}$ (in the formula, $R^{12}$ and $R^{13}$ are as described above);
(E5) an amido group represented by —$R^{18}$—$NR^{19}COR^{20}$ (in the formula, $R^{18}$ represents a substituted or unsubstituted, straight or branched divalent hydrocarbon group having from 2 to 20 carbons; $R^{19}$ represents a hydrogen atom or a substituted or unsubstituted, straight or branched monovalent hydrocarbon group having from 1 to 20 carbons; and $R^{20}$ represents a substituted or unsubstituted, straight or branched monovalent hydrocarbon group having from 1 to 30 carbons);
(E6) an amido group represented by —$R^{21}$—$CONR^{22}R^{23}$ (in the formula, $R^{21}$ represents a substituted or unsubstituted, straight or branched divalent hydrocarbon group having from 2 to 20 carbons; and $R^{22}$ and $R^{23}$ are each independently a hydrogen atom or a substituted or unsubstituted, straight or branched monovalent hydrocarbon group having from 1 to 20 carbons).

The definitions, types, or the like of the substituted or unsubstituted, straight or branched monovalent hydrocarbon groups and divalent hydrocarbon groups are as previously described.

On the other hand, the component (C1) may be an unsaturated aliphatic hydrocarbon. Examples of unsaturated aliphatic hydrocarbons include various dienes, diynes, enynes and similar products having two or more unsaturated bonds. In view of crosslinking, dienes, diynes, and enynes are preferable. Dienes, diynes, and enynes are compounds having a structure in which at least two unsaturated bonds are separated by one or more, and preferably two or more single bonds in a molecule. The unsaturated aliphatic hydrocarbon group may be present at the molecular terminal, or as a pendant group in the molecular chain.

The unsaturated aliphatic hydrocarbon as the component (C1) is exemplified by $\alpha,\omega$-unsaturated alkenes or alkynes having from 2 to 30 carbons. The component (C1) is exemplified by the (C1-1) $\alpha,\omega$-diene represented by general formula (2-1):

$$CH_2=CH(CH_2)_xCH=CH_2 \qquad (2\text{-}1)$$

(in the formula, $1 \leq x \leq 20$); the (C1-2) $\alpha,\omega$-diyne represented by general formula (2-2):

$$CH\equiv C(CH_2)_xC\equiv CH \qquad (2\text{-}2)$$

(in the formula, $1 \leq x \leq 20$); the (C1-3) $\alpha,\omega$-ene-yne represented by general formula (2-3):

$$CH_2=CH(CH_2)_xC\equiv CH \qquad (2\text{-}3)$$

(in the formula, $1 \leq x \leq 20$); and the (C1-4) bisalkenyl polyether compound represented by general formula (2-4):

$$C_mH_{2m-1}O(C_nH_{2n}O)_yC_mH_{2m-1} \qquad (2\text{-}4)$$

(in the formula, $2 \leq m \leq 20$; $3 \leq n \leq 4$; y is the total number of repetition of oxyethylene units, oxypropylene units, and oxybutylene units; and $1 \leq y \leq 180$).

Specific examples of the unsaturated aliphatic hydrocarbon of the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, 1-hexen-5-yne, or the like.

Component (C1) may be a single component, but may also be a mixture of two or more components having different structures. That is to say, the component (C1) may be a mixture of at least one type of organopolysiloxane and at least one type of unsaturated aliphatic hydrocarbon. Therefore, the expression "having an average of greater than one reactive unsaturated group" means that, when at least two types of organopolysiloxane and/or unsaturated aliphatic hydrocarbon are used, on average, there is more than one reactive unsaturated group per single molecule.

No particular limitation is placed on the structure of the (C2) organic compounds having at least one reactive unsaturated group and at least one epoxy group per single molecule as the component (C), as long as the organic compounds have a total of at least two, preferably from 2 to 10, further preferably from 2 to 7, yet further preferably from 2 to 5, and particularly preferably from 2 to 4 reactive unsaturated groups and epoxy groups in a single molecule. The utilized organic compound may have a straight, branched, or net-like structure. Moreover, the reactive unsaturated group included in (C2) may be a general unsaturated aliphatic hydrocarbon group such as an alkenyl group or the like, or may be a hetero atom-containing unsaturated aliphatic hydrocarbon group such as a methacryl group or the like. Preferred examples of the organic compound include organopolysiloxanes and unsaturated aliphatic epoxides. No particular limitation is placed on the position of the reactive unsaturated group in the organic compound, preferably the organopolysiloxane or unsaturated aliphatic epoxide, and this reactive unsaturated group may be located on the main chain or on the chain terminal. However, from the standpoint of ease of control of crosslinking density, a high purity compound is preferably used in which the total number of epoxy groups and reactive unsaturated groups in a single molecule is 2.

The reactive unsaturated group is preferably present in an unsaturated aliphatic hydrocarbon group. Examples of the unsaturated aliphatic hydrocarbon group are the same as previously described.

When the component (C2) is an organopolysiloxane, the reactive unsaturated group-containing unsaturated aliphatic hydrocarbon group and/or the epoxy group are preferably bonded to a silicon atom. Moreover, when the component (C2) is an organopolysiloxane, the groups other than the unsaturated aliphatic hydrocarbon group and/or the epoxy group bonded to the silicone atoms may be the previously described substituted or unsubstituted monovalent hydrocarbon groups or the reactive functional group-containing monovalent organic groups.

The component (C2) is preferably an unsaturated aliphatic epoxide having at least one epoxy group.

Examples of the component (C2) are
(C2-1) an unsaturated epoxy compound represented by general formula (2-6):

Formula 17

(2-6)

(in the formula, $R^4$ represents a substituted or unsubstituted, straight or branched monovalent hydrocarbon group having from 2 to 20 carbons that has one reactive unsaturated group); (C2-2) an unsaturated group-containing cycloaliphatic epoxy compound represented by the general formula (2-7):

General Formula (2-7):

Formula 18

(2-7)

(in the formula, $R^5$ represents a substituted or unsubstituted, straight or branched monovalent hydrocarbon group having from 2 to 20 carbons that has one reactive unsaturated group; $R^6$ represents a hydrogen atom or methyl group; and $R^7$ represents a hydrogen atom or methyl group). The definitions, classifications, or the like of the reactive unsaturated groups and the substituted or unsubstituted, straight or branched monovalent hydrocarbon groups in the aforementioned general formulae are the same as described previously.

Specific examples of the unsaturated aliphatic epoxide as the component (C2) include an allyl glycidyl ether, methallyl glycidyl ether, 1-methyl-4-isopropenylcyclohexene oxide, 1,4-dimethylcyclohexene oxide, 4-vinylcyclohexene oxide, vinylnorbornene mono-oxide, dicyclopentadiene mono-oxide, butadiene mono-oxide, 1,2-epoxy-5-hexene, 1,2-epoxy-9-decene, and 2,6-dimethyl-2,3-epoxy-7-octene. Among these, 4-vinylcyclohexene oxide is preferable.

Component (C2) may be a single component, but may also be a mixture of two or more components having different structures.

The reaction for producing the glycerin derivative-modified organopolysiloxane elastomer of the present invention, preferably the mono-glycerin and/or diglycerin derivative-modified organopolysiloxane elastomer, may be performed by known methods in the presence or absence of a reaction solvent. The reaction between the Si—H group and the reactive unsaturated group in the present invention is a hydrosilylation reaction. Moreover, when the (C2) organic epoxide having at least one reactive unsaturated group and at least one epoxy group in the molecule is used to perform crosslinking, bonding due to the reaction between the reactive unsaturated group and the Si—H group and formation of ether bond by the self ring-opening polymerization between epoxy groups (cation polymerization reaction occurring in the presence of SiH groups and platinum catalyst) both occur, and crosslinks are formed. It is possible to further promote this reaction by using high energy beam irradiation (ultraviolet radiation or the like) or further adding a general cation polymerization catalyst.

No particular limitation is placed on the reaction solvent as long as the reaction solvent is non-reactive. The reaction solvent is exemplified by alcohol-based solvents such as ethanol, isopropyl alcohol, and the like; aromatic hydrocarbon-based solvents such as toluene, xylene, and the like; ether-based solvents such as dioxane, THF, and the like; aliphatic hydrocarbon-based solvents such as n-hexane, cyclohexane, n-heptane, cycloheptane, methylcyclohexane, and the like; and chlorinated hydrocarbon-based organic solvents such as carbon tetrachloride and the like. The below described oil agents may also be used as reaction solvents. When an oil agent is used as the reaction solvent, after the crosslinking reaction, the composition composed of the organopolysiloxane elastomer and the oil agent may be obtained directly. In addition, it is possible to use pulverization by mechanical force to readily obtain a particulate composition composed of mono-glycerin and/or diglycerin derivative-modified organopolysiloxane elastomer and oil agent, and preferably a paste-like composition.

The hydrosilylation reaction may be performed in the presence or absence of a catalyst, but preferably is performed in the presence of a catalyst because the reaction can be carried out at a low temperature and in a shorter period of time. Examples of the hydrosilylation reaction catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. A usage amount of the catalyst is about 0.5 to 1000 ppm in terms of platinum metal, when using a platinum catalyst.

A reaction temperature of the hydrosilylation reaction is typically from 30 to 150° C., and a reaction time is typically from 10 minutes to 24 hours, and preferably from 1 to 10 hours.

Due to the hydrosilylation reaction or the cation polymerization reaction of the epoxy group, the component (A) is crosslinked by the component (C), and the polysiloxane chains derived from the component (A) are linked by crosslinking part having the carbon-silicon bond derived from the component (C). Moreover, the component (A) is provided with glycerin derivative groups derived from the component (B), and it is possible in this manner to obtain the glycerin derivative-modified organopolysiloxane elastomer of the present invention.

Furthermore, although the glycerin derivative-modified organopolysiloxane elastomer of the present invention essentially has a structure linked by crosslinking part having the carbon-silicon bond derived from the component (C), a part of the glycerin derivative-modified organopolysiloxane elastomer of the present invention may have crosslinking parts due to Si—O—C bonds. When this structure has functional groups capable of condensation or exchange reaction (i.e. groups such as the silanol group, alkoxy group, and the like) in the components (A) to (C), if crosslinking conditions are severe (i.e. crosslinking can be formed between polysiloxane chains, and the like), it is possible to secondarily form such crosslinking by reactions such as partial reaction between hydroxyl groups in the glycerin derivative groups derived from the component (B) and the S—H groups of the component (A).

During production of the glycerin derivative-modified organopolysiloxane elastomer of the present invention, the component (A) and the component (B) may be reacted, followed by further reaction of the component (C) with the component (A). It is also possible to react the component (A) and the component (C), and then to further react the component (B) with the component (A).

In the case of reaction of the component (A) with the component (B) and then further reacting the component (C) with the component (A), the average value of the silicon-bonded hydrogen atoms per single molecule of the component (A) reactive with the reactive unsaturated group of the component (C) is preferably greater than or equal to 1.5. That is to say, the number of silicon-bonded hydrogen atoms per single molecule of the component (A) for reacting with the reactive unsaturated group in the component (C) constituting the crosslinking part on average is greater than or equal to 1.5, preferably is in a range of 2.0 to 5.0, and particularly preferably is in a range of 2.5 to 3.5.

During production of the glycerin derivative-modified organopolysiloxane elastomer of the present invention, in addition to the component (A), the component (B), and the component (C), (Q) an organic compound (other than the component (C2)) having one reactive unsaturated group within a single molecule may be further reacted. One type of component (Q) may be used, or two or more types of component (Q) may be used. The aforementioned reaction preferably may be performed consecutively in the presence of the hydrosilylation reaction catalyst. Further, the definitions, classifications, or the like of the reactive unsaturated group in the component (Q) are as described above.

For example, if the component (C) is further reacted with the component (A) after reaction between the component (A) and the component (B), the component (Q) may be reacted with the component (A) prior to reaction between the component (A) and the component (B), or the component (Q) may be reacted with the component (A) after reaction between the component (A) and the component (B), or the component (Q) may be reacted with the component (A) after reaction of the component (C).

For example, if the component (B) is further reacted with the component (A) after reaction between the component (A) and the component (C), the component (Q) may be reacted with the component (A) prior to reaction between the component (A) and the component (C), or the component (Q) may be reacted with the component (A) after reaction between the component (A) and the component (C), or the component (Q) may be reacted with the component (A) after reaction of the component (B).

Examples of the component (Q) include chain organopolysiloxanes that have one reactive unsaturated group in a single molecule or hydrocarbon compounds having one reactive unsaturated group in a single molecule.

The hydrocarbon compound having one reactive unsaturated group in the molecule is preferably a monounsaturated hydrocarbons having from 2 to 60 carbons and is more preferably a 1-alkene. Examples of the 1-alkene include 1-hexene, 1 octene, 1-decene, 1-undecene, 1-dodecene, 1-tridecene, 1-tetradecene, 1-hexadecene, 1-octadecene, and the like. Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

During production of the glycerin derivative-modified organopolysiloxane elastomer of the present invention, this organopolysiloxane elastomer obtained by hydrosilylation reaction between the component (A), component (B), component (C), and optional component (Q) is preferably further subjected to an acid treatment step by treatment using at least one type of acidic inorganic salt. It is possible to reduce odor of the glycerin derivative-modified organopolysiloxane elastomer by this step.

The odor reducing treatment may be performed by a method of acid treatment at a stage prior to formation of the glycerin derivative-modified organopolysiloxane elastomer (i.e. at a stage prior to crosslinking). However, due to consumption of Si—H groups by dehydrogenation reaction due to the presence of acid and water and alcoholic hydroxyl groups, even though odor reduction had been performed, it becomes difficult to then perform crosslinking later as per design. Therefore, acid treatment is more preferably performed after the formation of the elastomer.

The acidic inorganic salt is preferably water soluble, and particularly preferably is a solid at 25° C. Further, when 50 g of the inorganic salt is dissolved in 1 L of ion exchanged water, pH value at 25° C. of the solution of the water-soluble acidic inorganic salt is less than or equal to 4, preferably is less than or equal to 3.5, and further preferably is less than or equal to 2.0. In cases where the acidic inorganic salt is a solid at room temperature (25° C.), as may be required, the acidic inorganic salt may be readily removed by filtration. Moreover, if the acidic inorganic salt is water soluble, as may be required, the acidic inorganic salt may be readily rinsed using water. The value of pH for the present invention is the value of a sample aqueous solution measured using a pH meter equipped with a glass electrode at room temperature (25° C.).

According to the present invention, odor of the organopolysiloxane elastomer is effectively reduced by use of the acidic inorganic salt without cutting the carbon-oxygen bonds or silicone-oxygen bonds, and it is possible to suppress the generation of odor that occurs due to the passage of time or the blend system.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the acidic inorganic salt is preferably at least one type of acidic inorganic salt comprising a hydrogen sulfate ion ($HSO_4^-$) or a hydrogen sulfite ion ($HSO_3^-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion.

Specific examples of the acidic inorganic salt include lithium hydrogen sulfate, sodium hydrogen sulfate, potassium hydrogen sulfate, rubidium hydrogen sulfate, cesium hydrogen sulfate, ammonium hydrogen sulfate, sodium hydrogen sulfite, hydrates of such salts, and Lewis acids such as $AlCl_3$, $FeCl_3$, $TiCl_4$, $BF_3.Et_2O$, and the like. For several acidic inorganic salts, the pH values of aqueous solutions when 50 g of the acidic salt is dissolved in 1 L of ion exchanged water are shown in the table below. From the perspective of the technical benefit of reducing odor, the water soluble acidic inorganic salt having a pH of not higher than 2.0 is preferably at least one type of acidic inorganic salt selected from the group consisting of sodium hydrogen sulfate, potassium hydrogen sulfate, and ammonium hydrogen sulfate.

TABLE 1

| Acidic inorganic salt | pH (50 g/L) |
| --- | --- |
| Sodium hydrogen sulfate | 1.5 or lower |
| Potassium hydrogen sulfate | 2.0 or lower |
| Ammonium hydrogen sulfate | 1.5 or lower |
| Sodium hydrogen sulfite | 3.5 |

The acid treatment step may be performed by contacting the organopolysiloxane elastomer with the acidic inorganic salt according to a desired embodiment.

Specifically, the acid treatment step may be performed by an operation of addition of at least one type of the acidic inorganic salt, together with water or a desired organic solvent such as alcohol or the like, to a reaction system (e.g. reaction vessel such as a flask or the like, or a mixing/powder crushing vessel, emulsification equipment, or the like) including the organopolysiloxane elastomer, and then stirring and mixing, kneading, crushing, or the like, or by repeating such processing. Alternatively and further preferably, the organopolysiloxane elastomer, or a composition including the organopolysiloxane elastomer and an oil agent, may undergo pulverization pre-treatment. Then, at least one type of the acidic inorganic salt is added, optionally together with water and an organic solvent such as an alcohol and the like, and the mixture is processed by heating and stirring, or the like.

Processing is particularly preferably carried out by adding at least one type of the acidic inorganic salt and water to a reaction system including the organopolysiloxane elastomer, and then stirring or kneading and pulverizing using mechanical force while heating the mixture. Further, such treatment is preferably performed in the presence of a solvent such as a lower monohydric alcohol or the like. The acid treatment step can be carried out at any temperature and treatment time, and can be carried out at a temperature from 0 to 200° C., and more preferably from 50 to 100° C., for a reaction time of from 0.5 to 24 hours, and more preferably from about 1 to 10 hours. The utilized amount of the acidic inorganic salt may be selected appropriately according to the acid strength, treatment apparatus, treatment time, and treatment temperature. However, in the case of use of an acidic inorganic salt of intermediate acid strength (e.g. sodium hydrogen sulfate, potassium hydrogen sulfate, ammonium hydrogen sulfate, or the like), the concentration of the acidic inorganic salt relative to the organopolysiloxane elastomer of the present invention is preferably in a range of 100 to 10,000 ppm.

In the production method for the organopolysiloxane elastomer of the present invention, after the acid treatment step, there is preferably a heating and/or pressure reduction step (stripping step). The aforementioned heating and/or pressure reduction is capable of removing (stripping off) the low-boiling components, i.e. odor-causing substances. Moreover, after the stripping, it is possible to remove more odor-causing substances by again performing the acid treatment step. In cases where acidic inorganic salts are remaining in the reaction system at this time, it is advantageous that there is no need for further addition of the acidic inorganic salt, and it is permissible to add water alone. That is to say, the acid treatment step and stripping step may be each repeated two or more times with objects such as increasing the degree of deodorizing or the like.

The "low-boiling components" removed by the stripping step, in addition to substances thought to cause odor such as carbonyl compounds (propionaldehyde or the like), also includes volatile components such as the reaction solvent, water, or the like used in the synthesis of the organopolysiloxane elastomer.

Further, the stripping step may be performed prior to the acid treatment step.

Stripping can be performed using known reaction conditions; however, stripping under atmospheric pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream or under a water vapor stream. A specific example of the step of removal of low-boiling components is one in which a mono-glycerin and/or diglycerin derivative-modified organopolysiloxane elastomer containing the low-boiling components or a composition of such is placed in a flask having a refluxing condenser, a nitrogen injection port, or the like; and nitrogen gas is supplied, the internal pressure is reduced and internal temperature is increased, and the pressure and temperature are maintained at constant values so as to remove the light substances. Here, typically, a pressure reduction parameter is from 0.1 to 10.0 kPa, a heating temperature is from 50 to 170° C., and a treatment time is from 10 minutes to 24 hours.

According to the present invention, after the treatment step using the acidic inorganic salt, the organopolysiloxane elastomer may be neutralized by a basic substance. One type of basic substance may be used alone, or alternatively, two or more basic substance may be used. The basic substance is exemplified by inorganic bases such as sodium hydroxide, potassium hydroxide, calcium hydroxide, barium hydroxide, ammonia water, sodium hydrogen carbonate, and the like; basic buffering agents such as trisodium phosphate, tripotassium phosphate, sodium citrate, sodium acetate, and the like; and organic bases such as basic amino acids, amines, pyridines, and the like. An amount of the basic substance is preferably an amount needed to neutralize a reaction system comprising the organopolysiloxane elastomer but, as necessary, the amount of the basic substance may be adjusted to an amount by which weak acidity or weak alkalinity is obtained.

The glycerin derivative-modified organopolysiloxane elastomer of the present invention is preferably in the form of particles, and further preferably is in the form of solid particles.

This particulate glycerin derivative-modified organopolysiloxane elastomer may be simply obtained by use of mechanical force to pulverize the cured glycerin derivative-modified organopolysiloxane elastomer, and these solid particles of the organopolysiloxane elastomer may be obtained of a desired particle diameter by adjusting pulverization conditions by known methods. Furthermore, pulverization may be performed by mixing an oil agent with the organopolysiloxane elastomer before or after primary pulverization, and then using mechanical force to perform primary pulverization or finer secondary pulverization of this organopolysiloxane elastomer in a dispersed or swollen state due to the oil agent.

No particular limitation is placed on the mechanical means used for pulverizing the glycerin derivative-modified organopolysiloxane elastomer or composition. However, the pulverization method is preferably at least one method selected from methods such as shearing, kneading, or passing through an orifice under pressure.

On the other hand, an aqueous dispersion of the organopolysiloxane elastomer particles can be obtained by emulsifying/dispersing in water the glycerin derivative-modified organopolysiloxane elastomer raw material composition prior to curing, and then crosslinking the emulsion, and it is possible to then obtain these organopolysiloxane elastomer particles by removing water from the aqueous dispersion and drying the organopolysiloxane elastomer particles.

No particular limitation is placed on the diameter of the glycerin derivative-modified organopolysiloxane elastomer particles, and this diameter may be selected according to application and feel. However, from the standpoint of formulation of the below described composition with the oil agent, volume average particle diameter as measured using microscopic observation or a particle diameter distribution measurement apparatus is preferably in a range of 20 to 1,000 μm, and further preferably is in a range of 25 to 300 μm.

(Composition Including the Glycerin Derivative-Modified Organopolysiloxane Elastomer)

The present invention also relates to a composition that includes the glycerin derivative-modified organopolysiloxane elastomer. No particular limitation is placed on the blended amount of the glycerin derivative-modified organopolysiloxane elastomer in the composition. For example, this blended amount relative to the total weight (mass) of the composition is in a range of 5 to 80 wt. % (mass %), preferably is in a range of 10 to 60 wt. % (mass %), further preferably is in a range of 15 to 50 wt. % (mass %), yet further preferably is in a range of 20 to 40 wt. % (mass %), and most preferably is in a range of 25 to 35 wt. % (mass %).

The composition of the present invention may further comprise at least one type of oil agent in addition to the organopolysiloxane elastomer. No particular limitation is placed on the oil agent, and a solid, semisolid, or liquid oil agent may be used. Specific examples include one type or two or more types of oil agent selected from silicone oils, hydrocarbon oils, ester oils, vegetable oils and fats, animal oils and fats, fatty acids, higher alcohols, triglycerides, artificial sebums, and fluorocarbon type oil agents. For these specific examples, as described in the patent application for which priority right is asserted for Japanese Patent Application No. 2011-121097 (relating to a sugar alcohol-modified silicone elastomer), the glycerin derivative-modified organopolysiloxane elastomer of the present invention is capable of maintaining stably various types of powders dispersed in an oil phase including such silicone oils or the like. Moreover, from the standpoint of improvement of environmental suitability and switching to a PEG-free formulation for the overall composition of the cosmetic or external use preparation, an oil agent is preferably selected that has a non-POE (polyoxyethylene) structure.

No particular limitation is placed on the blended amount of the oil agent in the composition of the present invention. For example, this blended amount relative to the total weight (mass) of the composition is in a range of 20 to 95 wt. % (mass %), preferably is in a range of 40 to 90 wt. % (mass %), further preferably is in a range of 50 to 85 wt. % (mass %), still further preferably is in a range of 60 to 80 wt. % (mass %), and most preferably is in a range of 65 to 75 wt. % (mass %).

Due to having a hydrophobic silicone chain and a hydrophilic glycerin derivative group, the glycerin derivative-modified organopolysiloxane elastomer of the present invention functions as a surfactant or emulsifier. Thus, the composition including the glycerin derivative-modified organopolysiloxane elastomer of the present invention and at least one type of oil agent may be in the form of an emulsion. No particular limitation is placed on the emulsion form, and any desired form may be used, such as an aqueous-oil type emulsion composition such as an oil-in-water emulsion, water-in-oil emulsion, and the like; or an oil-in-alcohol emulsion, alcohol-in-oil emulsion (e.g. polyol as the alcohol), or the like.

The average particle diameter of the emulsion particle emulsified by the glycerin derivative-modified organopolysiloxane elastomer of the present invention may be measured by a known measurement apparatus using the laser diffraction method, laser scattering method, or the like. The emulsion composition of the present invention is preferably a polar solvent-in-oil type emulsion, although an oil-in-polar solvent type emulsion is also permissible. Moreover, the emulsion may be a transparent micro-emulsion having a measured average particle diameter less than or equal to 0.1 μm, or the emulsion may be a milky emulsion of large particle diameter where the average particle diameter exceeds 10.0 μm. Furthermore, the emulsion particles may be micronized for the purpose of improving the stability and transparency of the appearance of the emulsion. An emulsion having a particle diameter from 0.5 to 20 μm can be selected for the purpose of improving sensation during use and adhesion characteristics to hair and skin.

The aforementioned emulsion or the like may be produced by mixing with water by use of mechanical forced using an apparatus to mix the glycerin derivative-modified organopolysiloxane elastomer of the present invention, or the composition including the glycerin derivative-modified organopolysiloxane elastomer of the present invention. The mixing apparatus is exemplified by a homomixer, paddle mixer, Henschel mixer, homo-disper, colloid mill, propeller stirrer, homogenizer, in-line continuous emulsification device, ultrasonic emulsification device, vacuum kneader, or the like. Moreover, the utilized amounts and blend ratios of water in the method for producing the emulsion composition are as described above. According to the form of the emulsion and the application of the emulsion, the amount in the entire emulsion composition may be selected appropriately in a range of 1 to 99 wt. % (mass %).

The composition of the present invention, which includes at least one type of oil agent in addition to the organopolysiloxane elastomer, may be used in the form of a paste. The glycerin derivative-modified organopolysiloxane elastomer blended in the composition of the present invention is preferably in the form of particles. Although any blending ratio (weight (mass) ratio) with the oil agent may be used, from the standpoint of obtaining a paste-like composition formed from fine and uniform particles that are free of the sensation of a foreign body, this blending ratio is preferably in a range of 5/95 to 50/50, particularly preferably is in a range of 10/90 to 40/60, and most preferably is in a range of 15/85 to 30/70. In particular, when the organopolysiloxane elastomer swells due to a mass of the oil agent at least the same as the mass of the organopolysiloxane elastomer itself, the organopolysiloxane elastomer is readily made to swell using an amount of the oil agent at least that of the organopolysiloxane elastomer, and preferably a paste-like composition may be readily prepared.

The composition including the oil agent and the particulate organopolysiloxane elastomer may be obtained by pulverizing the organopolysiloxane elastomer using mechanical force and then mixing with the oil agent. Alternatively, a mixture of the organopolysiloxane elastomer and the oil agent may be pulverized using mechanical force to obtain the composition including the oil agent and the particulate organopolysiloxane elastomer.

The composition of the present invention may include water. No particular limitation is placed on the blended amount of water in the composition of the present invention. For example, this blended amount relative to the total amount (mass) of the composition is in a range of 1 to 90 wt. % (mass %), preferably is in a range of 5 to 80 wt. % (mass %), further preferably is in a range of 10 to 70 wt. % (mass %), still further preferably is in a range of 20 to 60 wt. % (mass %), and most preferably is in a range of 30 to 50 wt. % (mass %).

The composition of the present invention may further comprise at least one type of alcohol. The alcohol is preferably an alcohol capable of mixing with water. The alcohol is further preferably a lower alcohol or polyhydric alcohol. Specific examples and utilized amounts of the alcohol are as described in the other patent application for which priority right is asserted based on Japanese Patent Application No. 2011-121097 (relating to a sugar alcohol-modified silicone elastomer). From the standpoint of improving environmental suitability and switching to a PEG-free formulation for the overall composition of the cosmetic or external use preparation, the alcohol is preferably selected from non-polyether structure polyhydric alcohols and/or lower monohydric alcohols.

The glycerin derivative-modified organopolysiloxane elastomer of the present invention or the composition including the glycerin derivative-modified organopolysiloxane elastomer of the present invention has fundamentally little tendency to oxidize and change in properties due to oxidation by oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT (2,6-di-t-butyl-p-cresol), vitamin C, vitamin E, or the like, will result in a further increase in stability. In this case, an added amount of the antioxidant that is used is in a range (by weight (mass)) from 10 to 1,000 ppm, and preferably from 50 to 500 ppm, of the organopolysiloxane elastomer.
(External Use Preparation Raw Material or Cosmetic Raw Material)

The glycerin derivative-modified organopolysiloxane elastomer of the present invention or the composition including the glycerin derivative-modified organopolysiloxane elastomer of the present invention may be used appropriately as an external use preparation raw material or cosmetic raw material used for the human body. In particular, a paste-like composition including the oil agent and the particulate organopolysiloxane elastomer of the present invention may be used without modification as the external use preparation raw material or cosmetic raw material.

The proportion of organopolysiloxane elastomer or the proportion of the composition containing the organopolysiloxane elastomer in the external use preparation raw material or cosmetic raw material relative to the raw material (total weight (mass) basis) is preferably from 10 to 50 wt. % (mass %), further preferably is from 15 to 40 wt. % (mass %), and most preferably is from 20 to 30 wt. % (mass %). A proportion of the raw material compounded in the external use preparation or the cosmetic is not particularly limited but, for example, can be from 0.1 to 90 wt. % (mass %), and is preferably from 1 to 80 wt. % (mass %), more preferably from 2 to 70 wt. % (mass %), and even more preferably from 5 to 50 wt. % (mass %) based on the total weight (mass) of the external use preparation or the cosmetic.

The external use preparation raw material or cosmetic raw material of the present invention is exemplified by oil phase gelling agents, oil phase structuring agents, oil phase thickeners, texture modifiers, humectants, masking agents such as wrinkle concealment agents or the like, surfactants, emulsifiers, and powder dispersion stabilizers.

External Use Preparation and Cosmetic

The glycerin derivative-modified organopolysiloxane elastomer of the present invention, the composition including the glycerin derivative-modified organopolysiloxane elastomer of the present invention, or the external use preparation or cosmetic raw material including the glycerin derivative-modified organopolysiloxane elastomer or the composition comprising the same may be suitably blended in an external use preparation or cosmetic, and it is possible to form an external use preparation or cosmetic of the present invention. Also, the external use preparation or cosmetic of the present invention is preferably contained in a container produced from a thermoplastic substance or a non-thermoplastic substance. Moreover, the container may have at least one compartment, and a unit for an external use preparation or for cosmetic use may be constituted using this container and the cosmetic or external use preparation of the present invention. Also, the external use preparation or cosmetic of the present invention may be used appropriately for a keratin-type substance such as skin, hair, or the like as a non-medical beautifying method mainly in order to apply a cosmetic (makeup) or care product (e.g. treatment for dry skin).

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic, for example, is preferably a skin external use preparation or skin cosmetic, skincare cosmetic, sun care cosmetic, anti-perspirant, foundation, colored cosmetic, external use preparation for hair, or hair cosmetic.

The skin external use preparation or skin cosmetic of the present invention includes the glycerin derivative-modified organopolysiloxane elastomer of the present invention or includes the composition including the glycerin derivative-modified organopolysiloxane elastomer of the present invention. No particular limitation is placed on the form of the skin external use preparation or skin cosmetic of the present invention, and this form is exemplified by a liquid, cream-like, solid, semi-solid, paste-like, gel-like, powder-like, multi-layer, mousse-like, and spray. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

In the same manner, the hair external use preparation or hair cosmetic of the present invention includes the glycerin derivative-modified organopolysiloxane elastomer of the present invention or includes the composition including the glycerin derivative-modified organopolysiloxane elastomer of the present invention; and various forms nay be used. For example, the hair external use preparation or the hair cosmetic of the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair external use preparation or the hair cosmetic of the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

Within a range such that the effect of the present invention is not impeded, components normally used in external use preparations or cosmetics may be added to the external use preparation or cosmetic of the present invention. The components that may be added are exemplified by water, powders or colorants, alcohols, water-soluble polymers, film forming agents, oil agents, oil soluble gelling agents, organomodified clay minerals, surfactants, resins, cosmetically permissible media, fatty phases, film-forming polymers, fibers, UV radiation-blocking photo-protective systems, UV radiation absorption agents, humectants, preservatives, anti-microbial agents, perfumes, salts, antioxidants, pH adjustment agents, chelating agents, refreshing agents, anti-inflammatory agents, whitening-beautifying components (whitening agents, cell activation agents, rough skin improving agents, blood circulation promotion agents, skin astringents, anti-seborrhoeic agents, or the like), vitamins, amino acids, nucleic acids, hormones, clathrate compounds or the like, bioactive substances, pharmaceutically effective ingredients, and perfumes, without particular limitation. Specific examples, methods of use, object of blending, and utilized amounts of these cosmetic components are as described in the other patent application for which priority right is asserted based on Japanese Patent Application No. 2011-121097 (relating to a sugar alcohol-modified silicone elastomer). Moreover, from the standpoint of increasing environmental compatibility and switching to a PEG-free formulation for the entire composition of the cosmetic or external use preparation, a formulation is preferred in which the cosmetic raw materials are non-polyether structure type water-soluble polymers, surfactants, emulsifiers, film-forming agents, humectants, or the like.

The glycerin derivative-modified organopolysiloxane elastomer of the present invention or the composition including the glycerin derivative-modified organopolysiloxane elastomer of the present invention is preferably used in combination with an organic-based UV absorber. Generally, the organic-based UV absorber has high polarity and does not readily dissolve. Therefore, conventionally, it has been difficult to stably compound a desired (high) amount of the organic-based UV absorber in water-in-oil (W/O) emulsion cosmetic compositions. However, if the glycerin derivative-modified organopolysiloxane elastomer of the present invention is used as an emulsifier, and if an intermediate polarity oil (ester oil or the like) is jointly used as a binding agent, even if a low polarity oil (e.g., silicone oil, hydrocarbon oil, or the like) is included in the oil phase, it is possible to obtain a W/O emulsion cosmetic in which is stably blended a UV absorber, and it is possible to finely disperse the UV absorber in the preparation in a stable manner. This therefore results in a further excellent sun care effect. In this case, the glycerin derivative-modified organopolysiloxane elastomer of the present invention is preferably used in combination with a xylitol-modified silicone having a siloxane dendron structure and long-chain alkyl groups, or a diglycerin-modified silicone having a siloxane dendron structure and long-chain alkyl groups, as a secondary emulsification agent. In this case, the compounded amount of the organic-based UV absorber is preferably in a range of 0.1 to 10 mass % and the compounded amount of the binding agent is preferably in a range of 0.005 to 5 mass %.

[Combination with Other Silicone-Based Cosmetic Raw Materials]

In the external use preparation or cosmetic of the present invention, according to the form thereof and formulation, solid silicone resins, crosslinking organopolysiloxanes (other than the organopolysiloxane elastomer of the present invention), acryl silicone dendrimer copolymers, silicone raw rubbers (silicone rubbers), polyamide-modified silicones, alkyl-modified silicone waxes, and alkyl-modified silicone resin waxes may be further blended. The organopolysiloxane elastomer of the present invention is composed of a polysiloxane chain or the like as the main chain, has glycerin derivative groups that do not have an oxyalkylene structure having an average number of repetitions of an oxyalkylene unit of 2 or greater as hydrophilic groups, and further has long-chain alkyl groups or the like. Thus, compounding stability with such silicone-based compounds is excellent, and there is the advantage of being able to design a cosmetic that utilizes the characteristic feel of such silicone-based cosmetic raw materials.

Specific examples, methods of use, objects of blending, and utilized amounts of these silicone-based cosmetic raw materials are as described in the other patent application for which priority right is asserted based on Japanese Patent Application No. 2011-121097 (relating to a sugar alcohol-modified silicone elastomer). Similarly, the advantageous effects obtained when the organopolysiloxane elastomer of the present invention is combined with these silicone-based cosmetic raw materials are as described in the other patent application for which priority right is asserted based on Japanese Patent Application No. 2011-121097 (relating to a sugar alcohol-modified silicone elastomer). Moreover, from the standpoint of increasing environmental compatibility and switching to a PEG-free formulation for the entire composition of the cosmetic or external use preparation, a formulation is preferred that selects a combination with silicone-based cosmetic raw materials that do not include a polyether structure.

Additionally, in cases where the external use preparation or the cosmetic according to the present invention is an anti-perspirant, or depending on the purpose thereof, the external use preparation or the cosmetic can contain an anti-perspiration active component and/or a deodorant agent. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in cosmetics or external use preparations other than anti-perspirants and it goes without saying that they can be beneficially compounded in the cosmetic or external use preparation of the present invention.

Specific examples, methods of use, objects of blending, and utilized amounts of these anti-perspirant active components, deodorant agents, or the like are as described in the other patent application for which priority right is asserted based on Japanese Patent Application No. 2011-121097 (relating to a sugar alcohol-modified silicone elastomer).

(Carbonyl Value Measurement Method)

The degree of odor of the glycerin derivative-modified organopolysiloxane elastomer of the present invention or the composition including the same may be determined by the carbonyl value, which is measured from the degree of light absorption of a reaction liquid obtained by reaction with the glycerin derivative-modified organopolysiloxane elastomer of the present invention or the composition including the same and 2,4-dinitrophenylhydrazine (2,4-DNPH) in a reaction medium including at least one type of monohydric lower alcohol having from 1 to 4 carbons. Furthermore, in addition to a compound having a carbonyl group such as an aldehyde and a ketone, the "carbonyl compound" also includes a potential carbonyl compound such as an acetal, propenyl ether, or a similar compound that does not comprise a carbonyl group but generates a carbonyl group by decomposing under certain conditions.

Thus, in order to quantitatively determine the degree of odor of the glycerin derivative-modified organopolysiloxane elastomer of the present invention or the composition including the glycerin derivative-modified organopolysiloxane elastomer of the present invention, the carbonyl compound-containing organopolysiloxane elastomer or composition containing the organopolysiloxane elastomer and 2,4-dinitrophenylhydrazine are reacted in a reaction medium including at least one type of monohydric lower alcohol having from 1 to 4 carbons, and the carbonyl value may be measured for the organopolysiloxane elastomer or composition including the organopolysiloxane elastomer based on light absorption of the reaction liquid obtained from the reaction. Details and the specific measurement method are as described in the other patent application for which priority right is asserted based on Japanese Patent Application No. 2011-121097 (relating to a sugar alcohol-modified silicone elastomer). Here, the "carbonyl value" is the carbonyl content index value, and is a value obtained by converting the absorbance (absorbance at 430 nm or 460 nm) of the reaction solution, obtained by reacting 2,4-DNPH with the sample, to per 1 g of sample. Furthermore, the measurement of the carbonyl value is able to quantitatively measure carbonyl compounds accurately and easily, and this method thus has the advantage of being able to be used appropriately for the evaluation of odor of an external use preparation or cosmetic.

For the glycerin derivative-modified organopolysiloxane elastomer of the present invention or the composition including the glycerin derivative-modified organopolysiloxane elastomer of the present invention, the carbonyl value measured by the aforementioned method is preferably less than or equal to 2.5 Abs/g, further preferably is less than or equal to 1.6 Abs/g, and most preferably is less than or equal to 1.2 Abs/g.

[Industrial Field of Use]

The glycerin derivative-modified organopolysiloxane elastomer of the present invention or the composition including the glycerin derivative-modified organopolysiloxane elastomer of the present invention may be used with advantage as an external use preparation raw material or a cosmetic raw material. Odor is reduced for the glycerin derivative-modified organopolysiloxane elastomer of the present invention produced using the acid treatment step and the composition of the present invention including such an organopolysiloxane elastomer. Therefore, blending is possible with advantage in an external use preparation or cosmetic.

PRACTICAL EXAMPLES

Hereinafter, the present invention is described in detail with reference to practical examples and comparative examples, but it should be understood that the present invention is not limited to these practical examples. The viscosity (kinetic viscosity) values are measured at 25° C.

The present invention is described below using examples, but the present invention is not limited thereto. Further, in the below described composition formulae, the $Me_3SiO$ group (or $Me_3Si$ group) is represented as M, the $Me_2SiO$ group is represented as D, the $Me_2HSiO$ group (or $Me_2HSi$ group) is represented as $M^H$, the MeHSiO group is represented as $D^H$, the unit in which one of the methyl groups of M is modified by a substituting group is represented by $M^R$, the unit in which one of the methyl groups of D is modified by a substituting group is represented by $D^R$, and isopropyl alcohol is abbreviated as IPA.

Further, although the "production of silicone compound No. X" or the like are described in the below described practical examples and comparative examples, the obtained product is in the form of a mixture that includes the main component as well as minor amounts of unreacted raw materials, diluents, or the like.

Practical Example 1

Method for Producing Silicone Compound No. 1

74.5 g of methylhydrogenpolysiloxane represented by the average composition formula $MD_{43.2}D^H{}_{8.2}M$ and 13.9 g of hexadecene (α-olefin purity: 91.7%) were placed in a reactor. While the mixture was stirred under a nitrogen stream, 0.05 mL of a hexamethyldisiloxane solution of platinum-1,3-divinyl-1,1,3,3-tetramethyldisiloxane complex (Pt concentration: 0.45 wt. %) was added at 22° C., heat was generated, and temperature rose to 47° C.

Thereafter, the mixture was heated to 50 to 60° C., and the mixture was reacted for 2 hours. A small amount of the reaction liquid was sampled, and the degree of reaction was calculated based on the alkali decomposition gas generation method (i.e. decomposition of residual Si—H groups using a KOH ethanol/water solution, and calculation of degree of reaction based on volume of the generated hydrogen gas). It was found that a modified silicone intermediate represented by the formula $MD_{43.2}D^{R*11}{}_{3.2}D^H{}_{4.72}D^{OR}{}_{0.28}M$ was generated. Thereafter, a solution composed of 8.64 g of diglycerin monoallyl ether, 0.03 g of natural vitamin E, and 60 g of isopropyl alcohol (IPA) was added to the reaction mixture. Then, 0.10 mL of the platinum catalyst was further added, and the mixture was reacted for 5.5 hours at 50 to 60° C. Thereafter degree of reaction was checked by the same method, and it was found that a modified silicone intermediate represented by the average composition formula of $MD_{43.2}D^{R*11}{}_{3.2}D^{R*21}{}_{1.62}D^H{}_{3.10}D^{OR}{}_{0.28}M$ had been generated. Here, $R^{*11}$ and $R^{*21}$ are as described below. Moreover, $D^{OR}$ is a structural unit generated by dehydrogenation reaction with $D^H$ and an alcoholic hydroxyl group or moisture, and this is a Me(OR)SiO group is including a Si—O—C bond or Si—O—H bond.

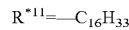
$R^{*11}$=—$C_{16}H_{33}$

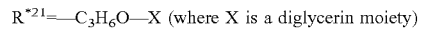
$R^{*21}$=—$C_3H_6O$—X (where X is a diglycerin moiety)

Next, 99 g of caprylyl methicone as a diluent and crosslinking reaction medium was added, and the reaction liquid was mixed. IPA was then removed by distillation under reduced pressure. At this time, the temperature of the reaction mixture was 45 to 55° C. Then, pressure was returned to atmospheric pressure, the mixture was cooled down to less than or equal to 50° C., and then 2.91 g of 1,5-hexadiene, and 0.14 mL of the platinum catalyst were added. When the mixture was stirred and heated at 40 to 50° C., gel formation occurred at 2 hours 15 minutes after addition of the catalyst. Furthermore, the Vi/H mole ratio of the crosslinking reaction was 1.20.

Furthermore, reaction was continued for 2 hours for further aging by heating to 50 to 60° C., and the production of the diglycerin derivative-modified organopolysiloxane elastomer according to the present invention was completed (production of 198 g of a composition including the diglycerin derivative-modified organopolysiloxane elastomer of the present invention and caprylyl methicone, elastomer concentration: 50%).

Thereafter, the composition was removed from the reactor, and this composition together with 352 g of caprylyl methicone were placed in a high shear mixer. Shearing and pulverizing treatment were performed for 30 minutes to obtain a uniform paste-like composition lacking in a sense of foreign objects when touched.

550 g of the uniform paste-like composition was placed in a reactor, and 0.022 g of sodium hydrogen sulfate monohydrate, 1.7 g of purified water, and 260 g of IPA were added. After mixing the mixture for 1 hour at 70 to 80° C., pressure was reduced, and the low-boiling components was removed by distillation (first acid treatment). Again, 1.7 g of purified water and 40 g of IPA were added, and the same treatment was performed. Then pressure was reduced, and the low-boiling components was removed by distillation (second acid treatment). This treatment was performed another time (third acid treatment), and then 10 g of 0.44% sodium bicarbonate aqueous solution was added, and the mixture was stirred to neutralize the mixture. Then the mixture was heated at 70 to 100° C. under reduced pressure to remove the low-boiling components by distillation to complete the odor reducing treatment of the diglycerin derivative-modified organopolysiloxane elastomer of the present invention and/or the paste-like composition including the diglycerin derivative-modified organopolysiloxane elastomer of the present invention.

Partial particle agglomeration occurred in the composition due to the acid treatment step. Thus the composition was removed from the reactor and placed again in the high shear mixer, and 30 minutes of shearing and pulverizing treatment were used to obtain a smooth and uniform paste-like composition that was entirely lacking in a sense of foreign objects when touched and included the diglycerin derivative-modified organopolysiloxane elastomer of the present invention (elastomer concentration: 18%).

The average structural formula (schematic drawing) of the organopolysiloxane elastomer obtained in Practical Example 1 is shown below. For simplicity, the structure corresponding to $D^{OR}$ has been omitted here:

Formula 19

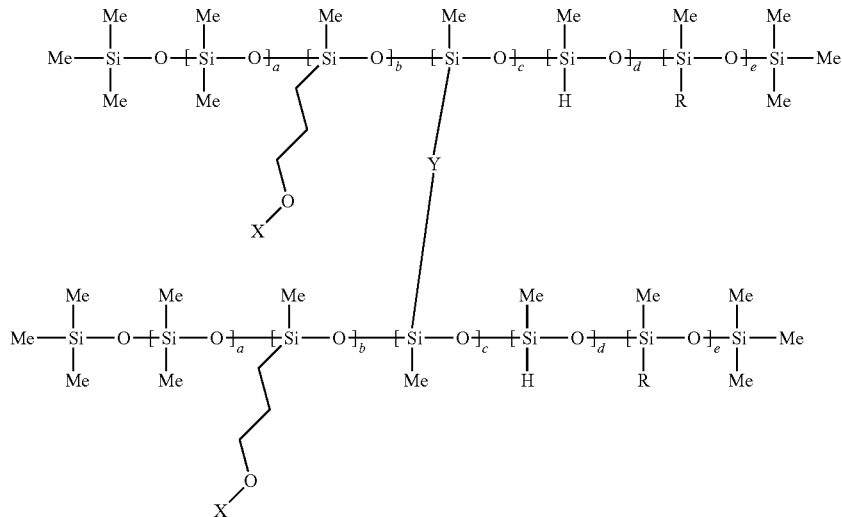

(in the formula, Me represents the methyl group; R represents $-C_{16}H_{33}$; Y represents $-C_6H_{12}-$; X represents $(C_3H_6O_2)_2H$; a=43.2; b=1.6; c+d=3.1; and e=3.2).

Practical Example 2

Method for Producing Silicone Compound No. 2

78.8 g of methylhydrogenpolysiloxane represented by the average composition formula $MD_{43.4}D^{H}_{7.4}M$, 21.5 g of diglycerin monoallyl ether, 60 g of IPA, 0.03 g of natural vitamin E, and 0.20 g of a 5% solution of sodium acetate in methanol were placed in a reactor, and heated to 40° C. while stirred under a nitrogen stream. 0.20 mL of a 1% solution of chloroplatinic acid in IPA was added. The mixture was heated to 60 to 70° C., and the mixture was reacted for 4 hours. A small amount of the reaction liquid was sampled, and the degree of reaction was calculated based on the alkali decomposition gas generation method. It was found that a modified silicone intermediate as represented by the formula $MD_{43.4}D^{R*21}_{4.66}D^{H}_{2.74}M$ was generated. Here, $R^{*21}$ has the below described meaning.

$R^{*21}=-C_3H_6O-X$ (X=diglycerin moiety)

Next, 99 g of caprylyl methicone as a diluent and cross-linking reaction medium was added, and the reaction liquid was mixed. IPA was then removed by distillation under reduced pressure. At this time, the temperature of the reaction mixture was 50 to 60° C.

Then pressure was returned to atmospheric pressure, the mixture was cooled down to 50° C., and then 2.78 g of 1,5-hexadiene, and 0.15 mL of the platinum catalyst were added. When the mixture was stirred and heated at 40 to 50° C., gel formation occurred at 50 minutes after addition of the catalyst. Furthermore, the Vi/H mole ratio of the crosslinking reaction was 1.22.

Furthermore, reaction was continued for 2 hours for further aging by heating to 50 to 60° C., and the production of the diglycerin derivative-modified organopolysiloxane elastomer according to the present invention was completed (production of 199 g of a composition including the diglycerin derivative-modified organopolysiloxane elastomer of the present invention and caprylyl methicone, elastomer concentration: 50%).

Thereafter, the composition was removed from the reactor, and this composition together with 200 g of caprylyl methicone were placed in a high shear mixer. Shearing and pulverizing treatment were performed for 30 minutes to obtain a composition (gel-in-oil particle mixture) lacking in a sense of foreign objects when touched.

390 g of the composition was placed in a reactor, and 0.02 g of sodium hydrogen sulfate monohydrate, 1.5 g of purified water, and 40 g of IPA were added. After mixing the mixture for 1 hour at 70 to 80° C., pressure was reduced, and the low-boiling components was removed by distillation (first acid treatment). Again, 1.7 g of purified water and 40 g of IPA were added, and the same treatment was performed. Then pressure was reduced, and the low-boiling components was removed by distillation (second acid treatment). This treatment was performed another time (third acid treatment), and then 10 g of 0.26% sodium bicarbonate aqueous solution was added, and the mixture was stirred to neutralize the mixture. Then the mixture was heated at 70 to 100° C. under reduced pressure to remove the low-boiling components by distillation to complete the odor reducing treatment of the diglycerin derivative-modified organopolysiloxane elastomer of the present invention and/or the gel-in-oil particle composition including the diglycerin derivative-modified organopolysiloxane elastomer of the present invention.

Partial particle agglomeration occurred in the composition due to the acid treatment step. Thus the composition was removed from the reactor and placed again in the high shear mixer, and 30 minutes of shearing and pulverizing treatment were used to obtain a smooth composition (gel-in-oil particle mixture) that was entirely lacking in a sense of foreign objects when touched and included the diglycerin derivative-modified organopolysiloxane elastomer of the present invention (elastomer concentration: 25%).

Practical Example 3

Method for Producing Silicone Compound No. 3

74.3 g of methylhydrogenpolysiloxane represented by the average composition formula $MD_{42.9}D^H{}_{9.8}M$ and 12.8 g of hexadecene (α-olefin purity: 91.7%) were placed in a reactor. While the mixture was stirred under a nitrogen stream, 0.05 mL of a hexamethyldisiloxane solution of platinum-1,3-divinyl-1,1,3,3-tetramethyldisiloxane complex (Pt concentration: 0.45 wt. %) was added at 24° C., heat was generated, and temperature rose to 44° C. Thereafter, the mixture was heated to 50 to 60° C., and the mixture was reacted for 1.5 hours. A small amount of the reaction liquid was sampled, and the degree of reaction was calculated based on the alkali decomposition gas generation method. It was found that a modified silicone intermediate as represented by the formula $MD_{42.9}D^{R*11}{}_{3.0}D^H{}_{6.61}D^{OR}{}_{0.19}M$ was generated. Thereafter, a solution composed of 10.0 g of glycerin monoallyl ether, 0.02 g of natural vitamin E, and 30 g of isopropyl alcohol (IPA) was added to the reaction mixture. Then, 0.10 mL of the platinum catalyst was further added, and the mixture was reacted for 2 hours at 50 to 60° C. Thereafter, degree of reaction was checked by the same method, and it was found that a modified silicone intermediate represented by the average composition formula of $MD_{42.9}D^{R*11}{}_{3.0}D^{R*22}{}_{3.6}D^H{}_{3.01}D^{OR}{}_{0.19}M$ had been generated. Here, $R^{*11}$ and $R^{*22}$ are as described below. Moreover, $D^{OR}$ is a structural unit generated by dehydrogenation reaction with $D^H$ and an alcoholic hydroxyl group or moisture, and this is a Me(OR)SiO group including a Si—O—C bond or Si—O—H bond.

$R^{*11}$=—$C_{16}H_{33}$ $R^{*22}$=—$C_3H_6OCH_2CH(OH)CH_2OH$

Next, 99 g of caprylyl methicone as a diluent and crosslinking reaction medium was added, and the reaction liquid was mixed. IPA was then removed by distillation under reduced pressure. At this time, the temperature of the reaction mixture was 50 to 60° C. Then pressure was returned to atmospheric pressure, the mixture was cooled down to 50° C., and then 2.79 g of 1,5-hexadiene, and 0.15 mL of the platinum catalyst were added. When the mixture was stirred and heated at 40 to 50° C., gel formation occurred at 2 hours after addition of the catalyst. Furthermore, the Vi/H mole ratio of the crosslinking reaction was 1.20.

Furthermore, reaction was continued for 2.5 hours for further aging by heating to 50 to 60° C., and the production of the monoglycerin derivative-modified organopolysiloxane elastomer according to the present invention was completed (production of 199 g of a composition including the monoglycerin derivative-modified organopolysiloxane elastomer of the present invention and caprylyl methicone, elastomer concentration: 50%).

Thereafter, the composition was removed from the reactor, and this composition together with 200 g of caprylyl methicone were placed in a high shear mixer. Shearing and pulverizing treatment were performed for 30 minutes to obtain a uniform paste-like composition lacking in a sense of foreign objects when touched. (elastomer concentration: 25%).

Note that the caprylyl methicone used in the Practical Examples 1 to 3 was manufactured by Dow Corning Toray Co., Ltd., product name=FZ-3196.

Comparative Example 1

Method for Producing Silicone Compound No. RE-1

125.3 g of methylhydrogenpolysiloxane represented by the average composition formula $MD_{40}D^H{}_{15}M$ and 13.7 g of 1-dodecene (corresponding to ¼ of the total added amount of 1-dodecene) were placed in a reactor. While the mixture was stirred under a nitrogen stream, the mixture was heated to 50° C., and 0.10 g of a solution of chloroplatinic acid in ethanol was added (Pt concentration: 3 wt. %). Temperature rose to 85° C. due to the reaction. After it was confirmed that temperature had naturally declined, 13.7 g of 1-dodecene was added for the second time, and the mixture was reacted. The same method was further used for third and fourth additions and reactions of 1-dodecene. Thereafter, the mixture was reacted for 1 hour at 90 to 100° C. A small amount of the reaction liquid was sampled, and it was confirmed that the target degree of reaction had been reached, based on the alkali decomposition gas generation method. Thereafter, the mixture was heated under reduced pressure, and the low-boiling components (unreacted dodecene or the like) were removed. Thereafter, 28.9 g of vinylmethylpolysiloxane represented by the average composition formula $^{Vi}MD_6M$ and 0.10 g of the platinum catalyst were added to the reaction mixture, and reaction was performed for 2 hours at 90 to 100° C. Thereafter, the degree of reaction was checked by the same method to confirm that the target degree of reaction had been reached. As a result of calculation of the degree of reaction, it was understood that a modified silicone intermediate as represented by the average composition formula $MD_{40}D^{R*41}{}_{1.5}D^{R*12}{}_{10}D^H{}_{3.5}M$ had been generated. Here, $R^{*12}$ and $R^{*41}$ have the same meanings as indicated above.

Then 20.9 g of bis-allyl triglycerin represented by the average composition formula $CH_2$=CH—$CH_2O$—$(C_3H_6O_2)_3$—$CH_2$—CH=$CH_2$ (or triglycerin diallyl ether), 0.025 g of natural vitamin E, 138 g of toluene, and 0.10 g of the platinum catalyst were added, and elastomer formation occurred after 2 hours of reaction at 80° C. The reaction mixture changed into a soft and sticky rice cake-like or jam-like form that seemed semi-transparent. In this case, the Vi/H molar ratio when crosslinking was 1.2. In order to promote crosslinking, reaction was continued for 2 hours under these conditions. This resulted in increased hardness, and the mixture became grease-like and had disintegrating property and a dry feel. Thereafter, the mixture was heated under reduced pressure, and the toluene was removed.

Next, 25.3 g of a 2% aqueous solution of citric acid was added, and treatment was performed for 2 hours at 80° C. Thereafter, 2% sodium bicarbonate aqueous solution was added, and the neutralization treatment was carried out for 1 hour. The mixture was heated under reduced pressure to remove the low-boiling components by distillation, and an organopolysiloxane elastomer modified by a group having a triglycerin group/C12 alkyl group/straight polysiloxane structure was obtained. Thereafter, the elastomer was transferred to a Hobart mixer. Kneading and pulverizing treatment were performed for 3 hours to obtain a uniform, white greasy composition. Thereafter, the mixture was kneaded while adding 680 g of isododecane as a diluent gradually over 3 hours to obtain a semi-transparent to white soft paste-like composition (elastomer concentration: 25%).

Practical Examples 4 to 13 and Comparative Examples 2 to 5

Using the compositions obtained in Practical Examples 1 to 3 and in Comparative Example 1, water-in-oil emulsion compositions were prepared as shown in Tables 1 to 3 by the below described procedure, and viscosity was measured. Further, static stability (appearance and form), stability with respect to stress, emulsion particle diameter, emulsion particle stability, and sensual performance (feel and feel of use) were evaluated according to the evaluation criteria below. The results are shown in Tables 2 to 4. In the table, "parts" indicates "parts by weight (mass)".

Preparation Method for Water-in-Oil Emulsion Composition
1. An oil agent and the paste-like composition or powder-in-oil mixture as a surfactant agent (emulsification agent) were placed in a 200 mL container.
2. The mixture was stirred, and this composition was uniformly dispersed in the oil agent (oil phase or powder-in-oil dispersed phase A).
3. Table salt and ion exchanged water were placed in a separate container. The salt was dissolved by mixing using a spatula. Furthermore, 1,3-butylene glycol was mixed and dissolved therein (aqueous phase B).
4. The teeth of a homo-disper were immersed in the oil phase A, and after fixing of the container, while the mixture was stirred at 1,000 rpm, the aqueous phase B was poured into the oil phase A at nearly a constant rate over a time interval of 45 seconds.
5. Rotation speed of the homo-disper was raised up to 3,500 rpm, and mixing was continued for 2 minutes until the overall mixture became uniform.
6. Stirring was stopped, the oil component or the like attached to the inner wall of the container was scraped off by a spatula and was added to the emulsion, and the generated emulsion was mixed.
7. Mixing was carried out for 3 minutes by 3,500 rpm rotation of the homo-disper so that the entire mixture became uniform.

[Viscosity and Properties of the Emulsion]
1. Properties and fluidity of the water-in-oil emulsion composition obtained in the aforementioned manner were recorded.
2. At 25° C. temperature, viscosity measurement of this emulsion composition was performed using an E type viscometer. During such measurement, viscosity was measured using a 0.5 rpm rotation rate of the cone rotor of the viscometer.

[Emulsion Static Stability: Visual Appearance and Form]
For each of the water-in-oil emulsion compositions on the date of preparation, and also for each emulsion composition after being set aside for 1 month at 50° C. (28 g measured out into a 35 mL glass container and then tightly stoppered), visual appearance and form were observed. These were evaluated by the below described criteria.

⊚: The composition has a creamy to gel-like form that overall has a uniform matte feel even after the passage of time.
o: The composition has a creamy to gel-like form having a matte feel where nearly the major part is uniform even after the passage of time. There may be a slight amount of precipitate.
Δ: The oil phase or aqueous phase is somewhat separated from the emulsion after the passage of time.
x: An emulsion itself was not made initially, and phase separation occurred.

[Stability of the Emulsion with Respect to Stress]
⊚: When the cream is taken up by the fingers and applied to the back of the hand, even when the cream is pressed against the skin somewhat strongly and spread by the fingers, there is no generation whatsoever of water droplets.
Δ: Although, when cream is taken up by the fingers and simply placed on the back of the hand, water droplets are not generated, water droplets are somewhat generated while the cream is being spread by the fingers.
x: The cream breaks down simply due to being taken up by the fingers, and water droplets are generated. When the cream is applied on the back of the hand, simply by lightly spreading the cream using the fingers, large droplets suddenly appear (emulsion breaks down immediately).

Measurement of Emulsified Particle Size and Evaluation of Stability
For each of the water-in-oil emulsion compositions on the day after preparation, and for each emulsion composition after being set aside for 1 month at 50° C. (in the aforementioned manner, 28 g weighed out into a glass container and tightly stoppered), the range of distribution of particle diameter was visually determined by optical microscope observation (1,000×) and photographic imaging. Thereby, stability was evaluated by examining the initial emulsified particle size and the emulsified particle size over time. Furthermore, the emulsification efficiency improves as the diameter of the emulsion particles decreases, and it is possible from that standpoint to think of performance to be excellent for small emulsion particles. Note that notes were made in the tables when particle coalescence was observed.

⊚: The emulsion particle diameter was small, and there was little variation in particle diameter.
o: Although diameter of the emulsion particles was somewhat large, there was little variation in particle diameter.
Δ: Although some of the particles are thought to have coalesced so that the diameter of the emulsion particles increased, overall particle diameters are not large, and the emulsion system is being maintained.
x: Many particles were coalesced and emulsion was in the state of breaking down, or there was severe coalescence from the start.

Functionality Evaluation (Feel and Feel of Use)
When each of the water-in-oil emulsion compositions was used as a cosmetic, the feel of use during the period of initial application until when application was in progress, the feel of use during the latter half of application, and the skin feel after drying were evaluated. However, comparative sensual evaluations were made among samples using the same oil agent in the formulations, i.e. using 2 cs trioctanoin as the oil agent. Specifically:
1. 0.10 g of the water-in-oil emulsion composition was placed on a finger and spread on the back of the hand.

2. At this time, feel of water and thick velvety smoothness intrinsic to an elastomer, powdery feel, and moisture retention sensation, lack of sticky feel when dried, or the like were evaluated according to the below criteria when the composition was initially applied until application was in progress, during the latter half of application, and after drying of the composition.

[Feel: Initial Application Until During Application]

◎: The composition had extremely fresh feel and intrinsic thick smoothness. Further, the composition spread thinly and immediately to an extent that the composition would not be thought to be an emulsion including an elastomer.

o: A watery feel was obtained, and intrinsic thick smoothness was maintained. The balance between the oily part and aqueous part was good, and the moisture retention feel was good.

Δ: Although an extremely fresh feel was obtained initially, there was a slimy slippery feel. Alternatively, although there was little watery feel and a sensation of oiliness, intrinsic thick smoothness was maintained.

x: The composition did not feel smooth and thick, and there was a strong oily feel.

[Feel: Later Half of Application]

◎: There was excellent soft and powdery slippery feel, or alternatively, there was excellent smoothness with an intrinsic thick velvety sensation.

o: Intrinsic thick smoothness remained, and there was a moist and calm luxurious feel.

Δ: The feel was that of a general cream and somewhat sticky.

x Spreadability and smoothness were poor, and there was considerable sensation of resistance. Also, there was somewhat of a sticky feel.

[after Skin Application Feel: After Drying]

◎: There was a soft and powdery slippery feel, or alternatively, the thick intrinsic velvety smoothness was maintained without any sticky feel whatsoever. The light and slippery surface feel is extremely excellent.

o: Although there was a soft and powdery slippery feel, or alternatively, the thick intrinsic velvety smoothness was maintained, slight stickiness was felt.

Δ: Although there was somewhat of a soft and powdery slippery feel, or alternatively, the thick intrinsic velvety smoothness remained, there was somewhat of a sticky feel, or there was the feel of a film.

x: There was a strong sticky feel, and there was almost no sense of slipperiness.

TABLE 2

Table 2: Formulations and evaluation results of the water-in-oil emulsion compositions (Practical Examples 4 to 7 and Comparative Examples 2 and 3)

| | Practical Examples | | | | Comparative Examples | |
|---|---|---|---|---|---|---|
| Name of raw material | 4 | 5 | 6 | 7 | 2 | 3 |
| Practical Example 1 paste-like composition (elastomer concentration: 18%) | 11.1 | 11.1 | — | — | — | — |
| Practical Example 3 paste-like composition (elastomer concentration: 25%) | — | — | 8 | 8 | — | — |
| Comparative Example 1 paste-like composition (elastomer concentration: 25%) | — | — | — | — | 8 | 8 |
| Dimethylpolysiloxane (2 cst) | 13.9 | — | 17 | — | 17 | — |
| Trioctanoin | — | 13.9 | — | 17 | — | 17 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Emulsifier conc. (%) | 2 | 2 | 2 | 2 | 2 | 2 |
| Properties of emulsion | Creamy to gel-like | | | | Creamy to gel-like | |
| Fluidity of emulsion | none | | | | none | |
| Emulsion viscosity (mPas) | 25,800 | 153,000 | 27,500 | 250,000 | 107,000 | 233,000 |
| Static stability of the emulsion | ◎ | ◎ | ◎ | ◎ | ◎ | ◎ |
| Stress stability of the emulsion | ◎ | ◎ | ◎ | ◎ | X | X |
| Initial particle diameter distribution (μm) | 2-7 | 1-3.2 | 2-6 | 0.5-2.5 | 3-13 coalesced | 3-30 coalesced |
| Particle diameter distribution after time has passed (μm) | 2-7 | 1-3.4 | 2-6 | 0.5-2.8 | 3-20 coalesced | 3-40 coalesced |
| Emulsion efficiency, stability of particles | O | ◎ | O | ◎ | X | X |
| Feel: time of initial application until during application | O | O | Δ | Δ | Δ | Δ |
| Feel: latter half of application | O | O | Δ | Δ | X | X |
| After skin application feel: after drying | O | O | Δ | Δ | X | X |

TABLE 3

Formulations and evaluation results of the water-in-oil emulsion compositions
(Practical Examples 8 to 11 and Comparative Examples 4 and 5)

|  | Practical Examples | | | | Comparative Examples | |
| --- | --- | --- | --- | --- | --- | --- |
| Name of raw material | 8 | 9 | 10 | 11 | 4 | 5 |
| Practical Example 1 paste-like composition (elastomer concentration: 18%) | 11.1 | 11.1 | — | — | — | — |
| Practical Example 3 paste-like composition (elastomer concentration: 25%) | — | — | 8 | 8 | — | — |
| Comparative Example 1 paste-like composition (elastomer concentration: 25%) | — | — | — | — | 8 | 8 |
| Caprylyl methicone | 13.9 | — | 17 | — | 17 | — |
| Mineral oil | — | 13.9 | — | 17 | — | 17 |
| Sodium chloride | 0.5 | 0.5 | 0.5 | 0.5 | 0.5 | 0.5 |
| Purified water | 68.5 | 68.5 | 68.5 | 68.5 | 68.5 | 68.5 |
| 1,3-butylene glycol | 6 | 6 | 6 | 6 | 6 | 6 |
| Emulsifier conc. (%) | 2 | 2 | 2 | 2 | 2 | 2 |
| Properties of emulsion | Creamy to gel-like | | | | Separated | Creamy to gel-like |
| Fluidity of emulsion | none | | | | | none |
| Emulsion viscosity (mPas) | 25,500 | 33,800 | 27,500 | 44,800 | X | 155,000 |
| Static stability of the emulsion | ◎ | ◎ | ◎ | ◎ | X | ◎ |
| Stress stability of the emulsion | ◎ | ◎ | ◎ | ◎ | X | X |
| Initial particle diameter distribution (μm) | 2-6 | 2-6 | 2-6 | 2-7 | X | 4-40 coalesced |
| Particle diameter distribution after time has passed (μm) | 2-6 | 2-6 | 2-7 | 2-8 | X | 5-40 coalesced |
| Emulsion efficiency, stability of particles | ○ | ○ | ○~Δ | ○~Δ | X | X |

TABLE 4

Table 4: water-in-oil emulsion composition formulations and
evaluation results (Practical Examples 12 and 13)

|  | Practical Examples | |
| --- | --- | --- |
| Name of raw material | 12 | 13 |
| Practical Example 2 powder-in-oil mixture (elastomer concentration: 25%) | 8 | 8 |
| Dimethylpolysiloxane (2 cst) | 17 | — |
| Caprylyl methicone | — | 17 |
| Sodium chloride | 0.5 | 0.5 |
| Purified water | 68.5 | 68.5 |
| 1,3-butylene glycol | 6 | 6 |
| Emulsifier conc. (%) | 2 | 2 |
| Properties of emulsion | Emulsion to creamy | |
| Fluidity of emulsion | Good | |
| Emulsion viscosity (mPas) | 9,800 | 7,300 |
| Static stability of the emulsion | Δ | Δ |
| Stress stability of the emulsion | ◎ | ◎ |
| Initial particle diameter distribution (μm) | 2-7 | 2-8 |
| Feel: time of initial application until during application | ◎ | ◎ |
| Feel: latter half of application | ◎ | ◎ |
| After skin application feel: after drying | ◎ | ◎ |

The composition of Practical Example 2 had non-uniform properties in that pulverized gel particles or gel powder were present in the oil, and this composition was not a uniform paste-like composition such as those of the Practical Example 1 and Practical Example 3. Thus, for Practical Example 12 and Practical Example 13, the powder-in-oil mixture of this form or the hydrophilic silicone elastomer having such properties was shown to function as an emulsifier that was useful in being able to impart emulsified droplets of relatively small particle diameter under general emulsification conditions without the application of very strong shear force in the water-in-oil agent form. Emulsifying elastomers and pastes displaying such behavior have not been previously recognized, and this is one technical effect discovered according to the present invention.

According to previous knowledge, an emulsion-forming silicone elastomer swells by absorption of the external phase oil agent by the three-dimensional network of the silicone elastomer so that fluidity of the oil phase is lost, static stability of the emulsion system is maintained, and it is thus normal that fluidity of the emulsion becomes lost. On the other hand, the emulsions of Practical Example 12 and Practical Example 13, despite including an elastomer in the oil phase, were characterized in that when the emulsions were placed in a container and were tilted, the emulsions readily flowed. Furthermore, although fluidity is a property that is disadvantageous for stability, stability with respect to emulsion stress was quite excellent, and the feel of use was particularly excellent.

The composition of Practical Example 2, as a simple formulation in this testing, had a 50° C. static stability that was inferior to that of the other practical examples. However, the formulation of Practical Example 2 had sufficient practical utility for a formulation for an actual cosmetic or external use preparation. Specifically, it is known that thermal stability problems generally occur for a fluid W/O emulsion when the emulsion is not designed to have a viscosity of greater than or equal to 15,000 mPas at 25° C. Thus, as a countermeasure, it is possible to respond by adjusting the aqueous phase/oil phase ratio, combined use with a second emulsifier capable of increasing emulsion viscosity, or combined use of an appropriate amount of thickener or gelling agent for the oil phase. When the composition of Practical Example 2 is used, from the standpoint of utilizing fluidity, emulsified formulation thermal stability is preferably improved by the combined use of a non-elastomer type PEG-free hydrophilic silicone (e.g. diglycerin-modified silicone having long chain alkyl groups, or the like) as a secondary emulsifier.

The compositions of Practical Example 1 and Practical Example 3 surpassed the composition of Comparative Example 1 for all evaluated items. In particular, the effect of the composition of Practical Example 1 was quite excellent.

As explained previously, despite the glycerin derivative-modified organopolysiloxane elastomer not including polyether groups whatsoever, the glycerin derivative-modified organopolysiloxane elastomer that does not have as a hydrophilic group an oxyalkylene structure having an average number of repetitions of an oxyalkylene unit of 2 or greater of the present invention exhibited compatibility with various types of organic oils, not just with silicone oils, in an water-containing water-in-oil emulsion agent form; and it has become clear that an emulsion is provided that has excellent stability for a wide range of oil agent types. As made clear by the results of Comparative Examples 2 to 5, this is an accomplishment that was entirely unattainable by the polyglycerin-modified silicone elastomer (composition of Comparative Example 1) of the conventional technology.

Furthermore, the water-in-oil emulsion including the glycerin derivative-modified organopolysiloxane elastomer of the present invention has an excellent sense of moisture retention, has moist feel when applied to the skin, and simultaneously retains a suitable oil component. Thus, if this water-in-oil emulsion is used as an external use preparation or cosmetic, it is possible to anticipate effects such as suppression of transdermal moisture loss, protection of the skin due to such suppression, and nourishment of the skin. In addition, in a water-in-oil emulsion including the glycerin derivative-modified organopolysiloxane elastomer of the present invention, not only was the initial sensation of use intrinsic to a powdery elastomer (i.e. thick and smooth) confirmed for the initial period of application, but unexpectedly, this sensation was found to be maintained to the latter half of application and further until after the water-in-oil emulsion had dried. This type of performance is one feature of the product of the present invention that is not achieved by the conventional hydrophilic silicone elastomer. This is made clear by a comparison of Practical Examples 4 and 5 versus Comparative Examples 2 and 3.

However, the greatest unanticipated remarkable technical effect of the present invention is that, even though all of the above described excellent effects are realized by the glycerin derivative-modified organopolysiloxane elastomer of the present invention, which is simultaneously a hydrophilic polymer, surfactant, and emulsifier, the glycerin derivative-modified organopolysiloxane elastomer of the present invention has the difficult-to-believe property of lacking almost any sticky feel during the time interval from application to drying, and even after drying. Conventionally, improvements of emulsification performance or the like have resulted in worsening from the standpoint of feel. The existence of a general tradeoff between characteristics in this manner has been common technical knowledge for one skilled in the art, and this tradeoff had become a common belief. However, the glycerin derivative-modified organopolysiloxane elastomer of the present invention immediately eliminates this tradeoff relationship, and good performance is attained that greatly exceeds the expectations of one skilled in the art.

Even if the water-in-oil emulsion composition of the present invention is a creamy to gel-like composition lacking the property of movement, it is a fact that the composition feels soft, and values of actually measured viscosity are much lower than those of the water-in-oil emulsion compositions obtained in the comparative examples displaying the same property. This fact is thought to reflect the feature of the present invention product that is low stickiness. In addition, the excellent stability of the emulsified particles and the emulsions of the present invention product is a remarkable effect that exceeds the common beliefs and technical knowledge concerning conventional polyglycerin-modified silicone elastomers. By use of the present invention product, in addition to dramatically increasing convenience during design of the formulation and increasing the degree of freedom of formulation of the cosmetic or external use preparation, it is possible to substantially improve performance and the effect of a cosmetic or external use preparation. Thus the contribution of the present invention to social development is quite large, and it was confirmed that benefits and excellent technical advantage are provided that could not be anticipated by one skilled in the art.

As mentioned previously, the glycerin derivative-modified organopolysiloxane elastomer of the present invention is extremely useful as a gelling agent, structuring agent, thickener, viscosity modification agent, texture modifier, humectant, masking agent (wrinkle concealment agent), surfactant, emulsifier, coating agent, powder dispersion stabilization agent, or the like, and the performance of such agents has exceeded that of the conventional technology. Despite the glycerin derivative-modified organopolysiloxane elastomer of the present invention lacking a polyether group in the structure of the glycerin derivative-modified organopolysiloxane elastomer, the glycerin derivative-modified organopolysiloxane elastomer of the present invention may be used alone as an emulsifier for a water-in-oil emulsion, and the glycerin derivative-modified organopolysiloxane elastomer of the present invention is able to maintain the excellent intrinsic performance and feel of an elastomer.

Thus, there is no need for the glycerin derivative-modified organopolysiloxane elastomer of the present invention to be used in combination with a nonionic surfactant such as a hydrophilic silicone emulsifier or the like having a PEG structure, and it is possible to prepare a water-in-oil emulsion cosmetic or the like that has sufficient stability. It is thus possible to switch the formulation of the cosmetic or external use preparation to an entirely PEG-free formulation (i.e. a formulation not including compounds having a polyoxyethylene (PEG) structure). That is to say, by the use of the glycerin derivative-modified organopolysiloxane elastomer of the present invention, it is possible to execute a business strategy that has high environmental compatibility and is in accord with the world-wide trend of the cosmetic industry toward switching to completely PEG-free formulations in the compositions of products intended for the end consumer.

That is to say, in addition to it being possible to use the glycerin derivative-modified organopolysiloxane elastomer of the present invention more widely than the conventional polyglycerin-modified silicone elastomers used in the comparative examples, the glycerin derivative-modified organopolysiloxane elastomer of the present invention greatly increases value of the overall external use preparation or cosmetic.

Hereinafter, formulation examples of the cosmetic and the external use preparation according to the present invention are described, but it is understood that the cosmetic and the external use preparation according to the present invention are not limited to the types and compositions recited in these formulation examples. Note that in the formulation examples, all raw materials that are described with a product number are products commercially available from Dow Corning Toray Co., Ltd.

For the cosmetic and external use preparation of the present invention, the "Practical Examples, Paste-like Compositions" in the various formulation examples in the Japanese patent application (invention relating to sugar alcohol-modified silicone elastomers) submitted on the same date as the present application and for which priory right is asserted based on Japanese Patent Application No. 2011-121097 may be replaced by the paste-like composition of the present invention. Further, the organopolysiloxane elastomer of the present invention may be used in the specific cosmetic formulations 1 to 47 indicated in the below table.

TABLE 5

Formulation Example 1: W/O cream foundation
Formulation Example 2: W/O Liquid foundation
Formulation Example 3: W/O type compact foundation
Formulation Example 4: O/W/O type liquid foundation
Formulation Example 5: W/O makeup foundation
Formulation Example 6: Rouge
Formulation Example 7: Powder foundation
Formulation Example 8: W/O type compact foundation
Formulation Example 9: Eye shadow
Formulation Example 10: W/O type UV blocking cream
Formulation Example 11: W/O type UV blocking emulsion
Formulation Example 12: O/W type UV blocking cream
Formulation Example 13: W/O/W type cream
Formulation Example 14: O/W/O type emulsion
Formulation Example 15: Skincare emulsion
Formulation Example 16: Skin care cream
Formulation Example 17: Foundation
Formulation Example 18: O/W type sunscreen agent
Formulation Example 19: Powder eye shadow
Formulation Example 20: Rouge
Formulation Example 21: Mascara
Formulation Example 22: O/W cream
Formulation Example 23: O/W cream
Formulation Example 24: Stick type anti-perspirant
Formulation Example 25: Water-free roll-on type anti-perspirant
Formulation Example 26: Nonaqueous anti-perspirant deodorant stick composition
Formulation Example 27: W/O solid anti-perspirant stick composition
Formulation Example 28: W/O emulsion type anti-perspirant cream composition
Formulation Example 29: water-in-oil emulsion transparent anti-perspirant composition
Formulation Example 30: Nonaqueous stick-form anti-perspirant composition
Formulation Example 31: Hair conditioner
Formulation Example 32: Shampoo
Formulation Example 33: Hair cream (set type)
Formulation Example 34: Shampoo
Formulation Example 35: Hair conditioner
Formulation Example 36: Hair treatment, rinse type
Formulation Example 37: Hair treatment, leave-on type TABLE 5-continued Formulation Example 38: Hair mist
Formulation Example 39: Hair foam
Formulation Example 40: Hair spray
Formulation Example 41: Hair wax
Formulation Example 40: Hair cream
Formulation Example 43: Hair lotion
Formulation Example 44: Hair oil
Formulation Example 45: Oxidation type hair color
Formulation Example 46: Hair manicure
Formulation Example 47: Perm The specific details of these formulation examples are disclosed completely and in detail in a patent application corresponding to the present application (Japanese patent application asserting priority right based on Japanese Patent Application No. 2011-121097) and filed in Japan by the applicant of the present application on the same date as the present application as well as in the Japanese patent application (Japanese Patent Application No. 2011-121097) serving as the basis for the assertion of priority right for the patent application. These disclosures are herein incorporated by reference.

The invention claimed is:

1. A glycerin derivative-modified organopolysiloxane elastomer wherein:
   the glycerin derivative-modified organopolysiloxane elastomer is obtained by reaction of:
   (A) an organohydrogenpolysiloxane, wherein the organohydrogenpolysiloxane is selected from the group consisting of:
   (i) $R^1_3SiO(R^1_2SiO)_v(R^1SiHO)_wSiR^1_3$,
   (ii) $HR^1_2SiO(R^1_2SiO)_v(R^1SiHO)_zSiR^1_3$, and
   (iii) $HR^1_2SiO(R^1_2SiO)_v(R^1SiHO)_zSiR^1_2H$,
   wherein $R^1$ is each independently a monovalent organic group; v is 0 or a positive integer; w is a positive integer; and z is 0 or a positive integer;
   (B) a glycerin derivative group-containing organic compound having a reactive unsaturated group, wherein the glycerin derivative group-containing organic compound has a diglycerin derivative group represented by following general formula (5-1):

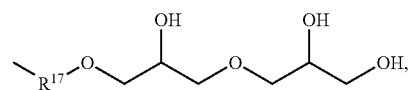

(5-1)

wherein $R^{17}$ represents an alkenyl group; and
   (C) at least one organic compound, wherein the organic compound is an am-diene represented by the general formula (2-1):

$$CH_2=CH(CH_2)_xCH=CH_2 \quad (2-1),$$

wherein $1<x<20$.

2. The glycerin derivative-modified organopolysiloxane elastomer according to claim 1, wherein the diglycerin derivative group is bonded to a silicon atom through a divalent linking group;
   the glycerin derivative-modified organopolysiloxane elastomer further comprising:
   another glycerin derivative group-containing organic group having an average number of repetitions of glycerin units in a range of 1.0 to 2.4, wherein the glycerin unit is at least one selected from the group consisting of glycerin units represented by the following structural formulae (4-1) to (4-3):

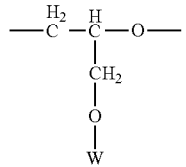
(4-1)

wherein, W is a hydrogen atom or an alkyl group having from 1 to 20 carbons;

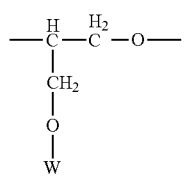
(4-2)

wherein, W is synonymous with the groups described above; and

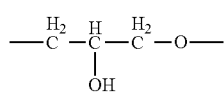
(4-3)

and, the another glycerin derivative group-containing organic group does not have as a hydrophilic group an oxyalkylene structure having an average number of repetitions of an oxyalkylene unit of 2 or greater.

3. The glycerin derivative-modified organopolysiloxane elastomer according to claim 1, wherein:
average value of the number of silicon-bonded hydrogen atoms per single molecule of the component (A) reactive with the reactive unsaturated group of the component (C) constituting the crosslinking part is greater than or equal to 1.5.

4. The glycerin derivative-modified organopolysiloxane elastomer according to claim 1, wherein:
the monovalent organic group $R^1$ is selected from the group consisting of (D1) to (D9):
(D1) substituted or unsubstituted, straight or branched monovalent hydrocarbon groups having from 1 to 60 carbons;
(D2) a polyoxyalkylene group represented by $-R^8O(AO)_zR^9$, wherein, AO represents an oxyalkylene group having from 3 to 4 carbons; $R^8$ represents a substituted or unsubstituted, straight or branched divalent hydrocarbon group having from 3 to 5 carbons; $R^9$ represents a substituted or unsubstituted, straight or branched monovalent hydrocarbon group having from 1 to 24 carbons, or a substituted or unsubstituted, straight or branched acyl group having from 2 to 24 carbons; and z=1 to 100;
(D3) a substituted or unsubstituted, straight or branched alkoxy group having from 1 to 30 carbons;
(D4) a hydroxyl group;
(D5) an ester group represented by $-R^{10}-COOR^{11}$, wherein, $R^{10}$ represents a substituted or unsubstituted, straight or branched divalent hydrocarbon group having from 2 to 20 carbons; and
$R^{11}$ represents a substituted or unsubstituted, straight or branched monovalent hydrocarbon group having from 1 to 30 carbons;
(D6) an ester group represented by $-R^{12}-OCOR^{13}$, wherein, $R^{12}$ represents a substituted or unsubstituted, straight or branched divalent hydrocarbon group having from 2 to 20 carbons; and
$R^{13}$ represents a substituted or unsubstituted, straight or branched monovalent hydrocarbon group having from 1 to 30 carbons;
(D7) an alkyl group substituted by a straight polysiloxane structure and represented by the following general formula (4):

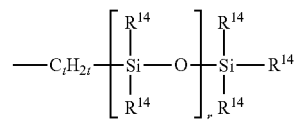
(4)

wherein, $R^{14}$ is each independently a substituted or unsubstituted, straight or branched monovalent hydrocarbon group having from 1 to 30 carbons, a hydroxyl group, or hydrogen atom, at least one of the $R^{14}$ moieties being the monovalent hydrocarbon group; t is a number in a range of 2 to 10; and r is a number in a range of 1 to 100;
(D8) an epoxy group represented by the following general formula (5):

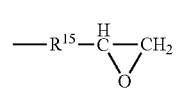
(5)

wherein, $R^{15}$ represents a substituted or unsubstituted, straight or branched divalent hydrocarbon group having from 2 to 20 carbons; and
(D9) an alicyclic epoxy group represented by the following general formula (6):

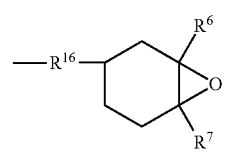
(6)

wherein, $R^{16}$ represents a substituted or unsubstituted, straight or branched divalent hydrocarbon group having from 2 to 20 carbons; $R^6$ represents a hydrogen atom or methyl group; and
$R^7$ represents a hydrogen atom or methyl group.

5. The glycerin derivative-modified organopolysiloxane elastomer according to claim 1, wherein
the glycerin derivative-modified organopolysiloxane elastomer is in the form of particles.

6. The glycerin derivative-modified organopolysiloxane elastomer according to claim 5, wherein volume average particle diameter of the particles is in a range of 20 to 1,000 μm.

7. The glycerin derivative-modified organopolysiloxane elastomer according to claim 1, wherein:
the glycerin derivative-modified organopolysiloxane elastomer is capable of swelling as a result of including a weight amount of an oil agent that is at least the weight of the glycerin derivative-modified organopolysiloxane elastomer itself.

8. A composition comprising:
the glycerin derivative-modified organopolysiloxane elastomer according to claim 1; and
at least one oil agent.

9. The composition according to claim 8, wherein the form of the composition is a paste.

10. The composition according to claim 8, wherein:
the composition is obtained by intermixing at least one oil agent after crushing the glycerin derivative-modified organopolysiloxane elastomer by use of mechanical force, or
by crushing a mixture of at least one oil agent and the glycerin derivative-modified organopolysiloxane elastomer, by use of mechanical force.

11. The composition according to claim 8, wherein the composition is an emulsion composition.

12. An external use preparation raw material comprising:
the glycerin derivative-modified organopolysiloxane elastomer according to claim 1.

13. The external use preparation raw material according to claim 12, wherein
the raw material is an agent selected from the group consisting of gelling agents, structuring agents, thickeners, texture modifiers, humectants, masking agents, surfactants, emulsifiers, coating agents, and powder dispersion stabilizers.

14. An external use preparation comprising the glycerin derivative-modified organopolysiloxane elastomer according to claim 1.

15. A method for producing the glycerin derivative-modified organopolysiloxane elastomer according to claim 1, the method comprising at least a step of reacting:
(A) an organohydrogenpolysiloxane, wherein the organohydrogenpolysiloxane is selected from the group consisting of:
(i) $R^1_3SiO(R^1_2SiO)_v(R^1SiHO)_wSiR^1_3$,
(ii) $HR^1_2SiO(R^1_2SiO)_v(R^1SiHO)_zSiR^1_3$, and
(iii) $HR^1_2SiO(R^1_2SiO)_v(R^1SiHO)_zSiR^1_2H$,
wherein $R^1$ is each independently a monovalent organic group; v is 0 or a positive integer; w is a positive integer; and z is 0 or a positive integer;
(B) a glycerin derivative group-containing organic compound having a reactive unsaturated group, wherein the glycerin derivative group-containing organic compound has a diglycerin derivative group represented by following general formula (5-1):

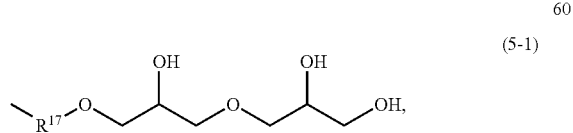

(5-1)

wherein $R^{17}$ represents an alkenyl group; and (C) at least one organic compound, wherein the organic compound is an α,ω-diene represented by the general formula (2-1):

$$CH_2\!\!=\!\!CH(CH_2)_xCH\!\!=\!\!CH_2 \qquad (2\text{-}1),$$

wherein $1 \leq x \leq 20$.

16. The method for producing the glycerin derivative-modified organopolysiloxane elastomer according to claim 15, wherein
a part or the entire reaction having the component (A), the component (B), and the component (C) is performed in the presence of at least one solvent selected from the group consisting of (P-1) and (P-2):
(P-1): an organic compound; and
(P-2): a compound having a silicon atom.

17. The method for producing the glycerin derivative-modified organopolysiloxane elastomer according to claim 15, wherein
the component (A) and the component (B) are reacted beforehand, and thereafter the component (C) is added to perform a crosslinking reaction;
the method further comprising a step selected from the group consisting of:
reacting a component (Q) with the component (A) prior to a reaction between the component (A) and the component (B);
after reaction of the component (A) and the component (B), further reacting the (Q) component; and
after crosslinking by the component (C), further reacting the component (Q),
wherein
(Q) is a compound having one reactive unsaturated group in a single molecule, with the exception of the organic compounds that have at least one reactive unsaturated group and at least one epoxy group per single molecule.

18. The method for producing the glycerin derivative-modified organopolysiloxane elastomer according to claim 15, wherein
the component (A) and the component (C) are reacted beforehand for introducing a crosslinking part, and thereafter the component (B) is added and reacted;
the method further comprising a step selected from the group consisting of:
reacting a component (Q) with the component (A) prior to reaction between the component (A) and the component (C);
after reaction of the component (A) and the component (C), further reacting the component (Q); and
after reaction with the component (B), further reacting the component (Q),
wherein
(Q) is a compound having one reactive unsaturated group in a single molecule, with the exception of the organic compounds that have at least one reactive unsaturated group and at least one epoxy group per single molecule.

19. A method for producing a glycerin derivative-modified organopolysiloxane elastomer including the step of:
treating the glycerin derivative-modified organopolysiloxane elastomer obtained by the method according to claim 15, using at least one acidic inorganic salt having the following properties:
being a solid at 25° C.,
being water soluble, and having a
pH at 25° C. of an aqueous solution upon dissolving of 50 g in 1 L of ion exchanged water being less than or equal to 4.

20. The method for producing a glycerin derivative-modified organopolysiloxane elastomer according to claim 19,
wherein the acidic inorganic salt is at least one acidic inorganic salt comprising a hydrogen sulfate ion ($HSO_4^-$) and a monovalent cation (M+).

21. The method for producing a glycerin derivative-modified organopolysiloxane elastomer according to claim 19, wherein
the acidic inorganic salt is at least one selected from the group consisting of sodium hydrogen sulfate, potassium hydrogen sulfate, and ammonium hydrogen sulfate.

22. The method for producing a glycerin derivative-modified organopolysiloxane elastomer according to claim 19, wherein a
utilized amount of the acidic inorganic salt relative to the glycerin derivative-modified organopolysiloxane elastomer is in a range of 100 ppm to 10,000 ppm.

23. The method for producing a glycerin derivative-modified organopolysiloxane elastomer according to claim 19, wherein
the treatment step using the acidic inorganic salt is performed in the presence of water and/or a hydrophilic medium.

24. The method for producing a glycerin derivative-modified organopolysiloxane elastomer according to claim 19, the method further comprising a step of removing low-boiling components by heating or reducing pressure after the treatment step using the acidic inorganic salt.

25. The method for producing a glycerin derivative-modified organopolysiloxane elastomer according to claim 19, the method further comprising a step of neutralizing by addition of at least one basic substance after the treatment step using the acidic inorganic salt.

* * * * *